(12) United States Patent
Mardor et al.

(10) Patent No.: US 11,931,569 B2
(45) Date of Patent: Mar. 19, 2024

(54) METHOD FOR CHANGING BLOOD BRAIN BARRIER PERMEABILITY

(71) Applicant: TEL HASHOMER MEDICAL RESEARCH, INFRASTRUCTURE AND SERVICES LTD., Ramat Gan (IL)

(72) Inventors: Yael Mardor, Netanya (IL); Shirley Sharabi, Ganei Tikva (IL); Itzik Cooper, Rehovot (IL); David Last, Jerusalem (IL); David Guez, Tel Aviv (IL); Dianne Daniels Elmakias, Ramat Hasharon (IL); Yael Bresler, Tel Aviv (IL)

(73) Assignee: TEL HASHOMER MEDICAL RESEARCH, INFRASTRUCTURE & SERVICES LTD., Ramat Gan (IL)

(*) Notice: Subject to any disclaimer, the term of this patent is extended or adjusted under 35 U.S.C. 154(b) by 16 days.

(21) Appl. No.: 16/980,104

(22) PCT Filed: Mar. 12, 2019

(86) PCT No.: PCT/IL2019/050276
§ 371 (c)(1),
(2) Date: Sep. 11, 2020

(87) PCT Pub. No.: WO2019/175871
PCT Pub. Date: Sep. 19, 2019

(65) Prior Publication Data
US 2021/0016084 A1    Jan. 21, 2021

Related U.S. Application Data

(60) Provisional application No. 62/641,522, filed on Mar. 12, 2018.

(51) Int. Cl.
*A61N 1/32* (2006.01)
*A61N 1/02* (2006.01)
(Continued)

(52) U.S. Cl.
CPC ............ *A61N 1/327* (2013.01); *A61N 1/025* (2013.01); *A61N 2/002* (2013.01); *A61N 2/02* (2013.01)

(58) Field of Classification Search
CPC ........ A61N 1/025; A61N 1/327; A61N 2/002; A61N 2/02
See application file for complete search history.

(56) References Cited

U.S. PATENT DOCUMENTS

| 8,992,517 | B2 | 3/2015 | Davalos et al. |
| 9,486,621 | B2 | 11/2016 | Howard et al. |

(Continued)

OTHER PUBLICATIONS

Christopher B. Arena, Brain Research; Focal blood-brain-barrier disruption with high-frequency pulsed electric fields, Aug. 31, 2014, pp. 1-2.

(Continued)

*Primary Examiner* — Christine H Matthews
(74) *Attorney, Agent, or Firm* — CANTOR COLBURN LLP

(57) ABSTRACT

A system and a method for increasing permeability of a brain barrier selected from a blood-brain barrier or a blood-cerebrospinal fluid barrier by controlled application of pulsed electric fields.

10 Claims, 13 Drawing Sheets

(51) Int. Cl.
*A61N 2/00* (2006.01)
*A61N 2/02* (2006.01)

(56) References Cited

U.S. PATENT DOCUMENTS

| | | |
|---|---|---|
| 2007/0020326 A1 | 1/2007 | Walker et al. |
| 2010/0137936 A1 | 6/2010 | Dennis et al. |
| 2011/0046540 A1* | 2/2011 | Alterman ............... A61N 1/044 |
| | | 604/501 |
| 2011/0106221 A1 | 5/2011 | Neal, II et al. |
| 2014/0039489 A1 | 2/2014 | Davalos et al. |
| 2014/0107426 A1 | 4/2014 | Wilson |
| 2017/0266438 A1 | 9/2017 | Sano et al. |

OTHER PUBLICATIONS

Paulo A. Garcia, 7.0-T Magnetic Resonance Imaging Characterization of Acute Blood-Brain-Barrier Disruption Achieved with Intracranial Irreversible Electroporation, PLOS One, Nov. 2012, vol. 7, Issue 11, pp. 1-8.

Mohammad Hjouj, MRI Study on Reversible and Irreversible Electroporation Induced Blood Brain Barrier Disruption, PLOS One, Aug. 2012, vol. 7, Issue 8, pp. 1-9.

S V Lopez-Quintero, DBS-relevant electric fields increase hydraulic conductivity of in vitro endothelial monolayers, Journal of Neural Engineering, Jan. 14, 2010, pp. 1-11.

Shirley Sharabi, A statistical model describing combined irreversible electroporation and electroporation-induced plood-brain barrier disruption, Radiol Oncol 2016; 50(1): pp. 28-38.

Shirley Sharabi, Dynamic effects of point source electroporation on the rat brain tissue, Bioelectrochemistry 2014, 99: pages 30-39.

Shirley Sharabi, Effect of Electroporation on Blood-Brain Barrier, Springer International Publishing Switzerland 2016 D. Miklavcic, Handbook of Electroporation, pp. 1-17.

Shirley Sharabi, Electroporation for the treatment of brain tumors, Thesis Submitted for the Degree "Doctor of Philosophy", Mar. 2017, pp. 1-106.

Search Report and Written Opinion for International Application dated Jul. 15, 2019, PCT application No. PCT/IL2019/050276, filed Mar. 12, 2019.

European Search Report dated Nov. 9, 2021 for application No. 19767293.4 filed Sep. 14, 2020.

* cited by examiner

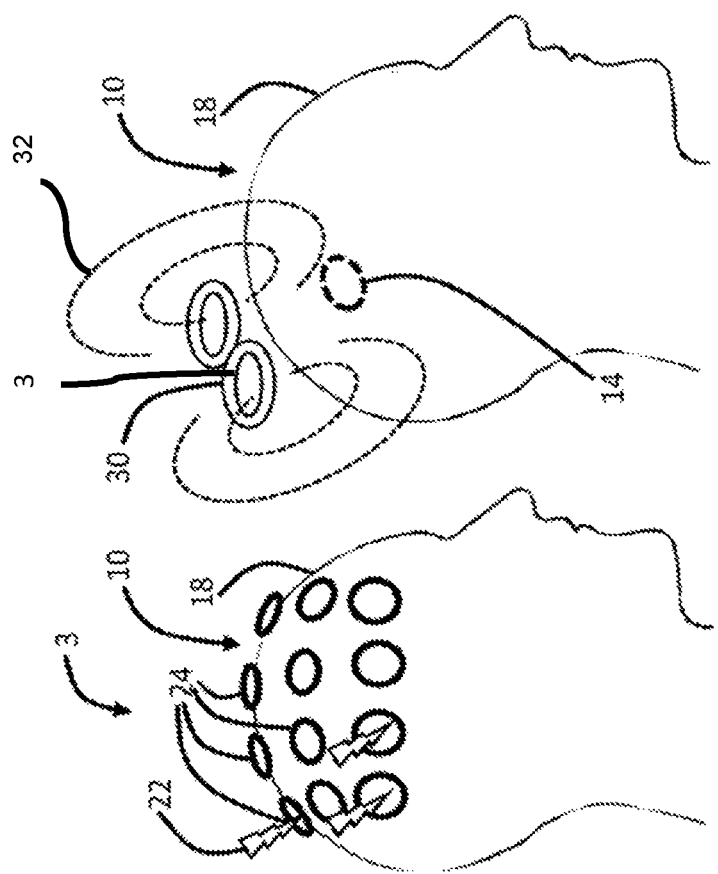
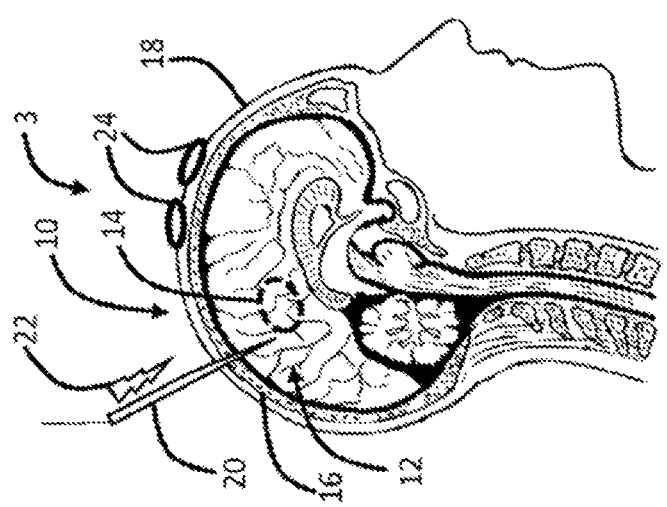
FIG. 1B   FIG. 1C   FIG. 1D

100V

200V

0V

150V

METHOD FOR CHANGING BLOOD BRAIN BARRIER PERMEABILITY

RELATED APPLICATIONS

This application is a US National Phase of PCT Application No. PCT/IL2019/050276, filed on Mar. 12, 2019, which claims benefit under 35 U.S.C. 119(e) of U.S. Provisional Application 62/641,522 filed Mar. 12, 2018. The contents and disclosure of the above-noted applications are incorporated herein by reference.

BACKGROUND

A blood brain barrier (BBB) is a multicellular vascular structure that separates the central nervous system (CNS) from peripheral blood circulation. The BBB composed of several cell types including the single-cell layer of endothelial cells (ECs) that form capillary walls of CNS blood vessels, as well as astrocytes and pericytes that surround the capillary walls. These cells together with neurons and microglia form the neuro-vascular unit (NVU). Blood vessel capillaries throughout CNS tissue (including brain, brainstem, and spinal cord) from a BBB. ECs of CNS blood vessels that form the BBB are different from ECs of blood vessels located in peripheral, non-CNS tissues. EC's of CNS blood vessels, unlike those in peripheral blood vessels, have continuous intercellular tight junctions (TJs) and adherens junctions (AJ) that lack fenestrations. TJs are composed of a branching network of sealing strands, each strand being formed from a row of transmembrane proteins embedded in both plasma membranes, with extracellular domains joining one another directly. Although more proteins are present, major protein types include claudins and occludins. An AJ is defined as a cell junction whose cytoplasmic face is linked to the actin cytoskeleton. They can appear as bands encircling the cell (zonula adherens) or as spots of attachment to the extracellular matrix (adhesion plaques). On the extracellular surface, AJs are typically composed of cadherins, a family of transmembrane proteins that form homodimers in a calcium-dependent manner with other cadherin molecules on adjacent cells. As such, the endothelium in CNS blood vessels acts as a 'physical barrier' limiting paracellular movement of molecules and a gate controlling molecular traffic into and out of CNS tissue.

The choroid plexus produces cerebrospinal fluid (CSF) in the ventricles of the brain. The choroid plexus comprises many blood vessel capillaries, separated from the ventricles by a single-cell layer of choroid epithelial cells. Fluid from the capillaries filters through the choroid epithelial cells to become cerebrospinal fluid. While ECs in the walls of blood capillaries at the choroid plexus do not form a BBB, the filtering process is highly regulated by the presence of a blood cerebrospinal fluid barrier (BCSFB). The BCSFB is formed by the choroid epithelial cells, which are connected via continuous intercellular TJs and AJs that lack fenestrations. This form of BCSFB may be referred herein as a "choroid plexus BCSFB". Another form a BCSFB, which may be referred to in the art as an "outer blood-CSF barrier" or a "meningeal barrier" is located in meningeal blood vessel capillaries that are located within subarachnoid space along a pia mater surface throughout the CNS, including along a pia mater surface of the brain, the brainstem, and the spinal cord. The meningeal barrier is formed by a single-cell layer of ECs forming the wall of meningeal blood capillaries, wherein the ECs have continuous intercellular TJs and AJs that lack fenestrations.

For convenience of presentation, BBB and BCSFB may be collectively referred to herein as a "brain barrier" or "BB". While BBs can serve to block entry of harmful agents, such as toxins, into brain tissue or the CSF, the BB also forms an obstacle for efficient drug delivery into the brain, making effective treatment of many brain diseases difficult or impossible.

SUMMARY

Thus, ways to disrupt a BB to increase its permeability in a controlled manner that is optionally localized and/or transient, are needed for efficient treatment of CNS diseases, including tumors formed in the CNS.

The present disclosure provides a method of increasing permeability of a BB in a targeted region of the CNS through application of pulsed electric fields (PEFs) in the targeted region. The BB is optionally a BBB or a BCSFB. The BCSFB is optionally a choroid plexus BCSFB or a meningeal barrier. The region of the CNS is optionally a region comprising one or more of: a brain, a brainstem, a spinal cord, and a choroid plexus.

An aspect of an embodiment of the disclosure relates to a method for treating a subject in need thereof, the method comprising: selecting a treatment region within a CNS of the subject, wherein an increased permeability of the BB at the treatment region is desired; and applying PEFs to at least a portion of the CNS that is capable of temporarily increasing permeability of the BB at the treatment region. In an embodiment of the disclosure, the applied PEFs are configured to not induce electroporation at or near the treatment region. Optionally the applied PEFs are configured to not induce electroporation anywhere in the CNS.

For convenience of presentation, increased permeability of the BB in a treatment region that does not require concomitant induction of electroporation in the treatment region may be referred to in the present application as "BB disruption". As such, a method in accordance with an embodiment of the disclosure for applying one or more PEFs to induce BB disruption at a desired treatment region may be referred to as a "BB disruption method", and PEFs capable of inducing BB disruption at the desired treatment region maybe referred to as "BB-disruptive PEFs". Optionally, BB-disruptive PEFs are applied before or after another set of PEFs configured to induce electroporation (reversible electroporation or irreversible electroporation) in the CNS region of the subject, optionally at the treatment region or elsewhere in the CNS. In an embodiment of the disclosure, BB disruption induced by application of BB-disruptive PEFs is temporary, and the increased BB permeability induced by PEF application reverses from the "open" state of relatively high permeability back to a default "closed" state of relatively low permeability.

In an embodiment of the disclosure, a BB-disruptive PEF train is characterized by an electric field ("EF") having a predetermined voltage-to-distance ratio (which may also be referred to herein as an "EF intensity" or "EF strength", optionally expressed in a unit of voltage per centimeter (V/cm)) being induced at the targeted treatment region. Optionally, the BB-disruptive PEF train is further characterized by a predetermined frequency and/or pulse count.

In an embodiment of the disclosure, the method further comprises administering a therapeutic agent to the subject in an amount sufficient to have the administered therapeutic agent be introduced in the bloodstream of the subject, wherein PEFs are capable of increasing permeability of the BB for the therapeutic agent to be delivered at the treatment region.

In an embodiment of the disclosure, the treatment region is a region of the CNS affected by a CNS disorder. Optionally, the treatment region comprises a CNS tumor, or a lesion or CNS region associated with an essential tremor, a stroke, an aneurism, hypoxia, or a neurodegenerative disease, by way of example Alzheimer's disease, Parkinson's disease, multiple sclerosis, amyotrophic lateral sclerosis, or Huntington's disease.

In an aspect of the disclosure, there is provided a BB disruption system comprising at least one EF source operatively connected to a power source and a signal generator. The signal generator is optionally controlled by a processor that is operable to instruct, in accordance with a set of instruction stored in a memory, to activate the EF source to produce BB-disruptive PEFs in accordance with an embodiment of the disclosure. Optionally, the at least one EF source comprises one or more electrodes. Optionally, the at least one EF source comprises a magnetic field source configured to generate a magnetic field, optionally a changing magnetic field, which then generates an EF by electromagnetic induction.

In some aspects of the disclosure, there is provided a method of treating a brain disease, by way of example a brain tumor or a neurodegenerative disease, which comprises a BB disruption method in accordance with an embodiment of the disclosure.

In the discussion, unless otherwise stated, adjectives such as "substantially", "relatively" and "about" modifying a condition or relationship characteristic of a feature or features of an embodiment of the disclosure, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the disclosure are described below with reference to figures attached hereto that are listed following this paragraph. Identical structures, elements or parts that appear in more than one figure are generally labeled with a same numeral in all the figures in which they appear. Dimensions of components and features shown in the figures are chosen for convenience and clarity of presentation and are not necessarily shown to scale.

FIGS. 1B-1D schematically illustrate optional embodiments of an EF source comprised in a BB disruption system in accordance to embodiments of the disclosure;

DETAILED DESCRIPTION

Figure 1A:
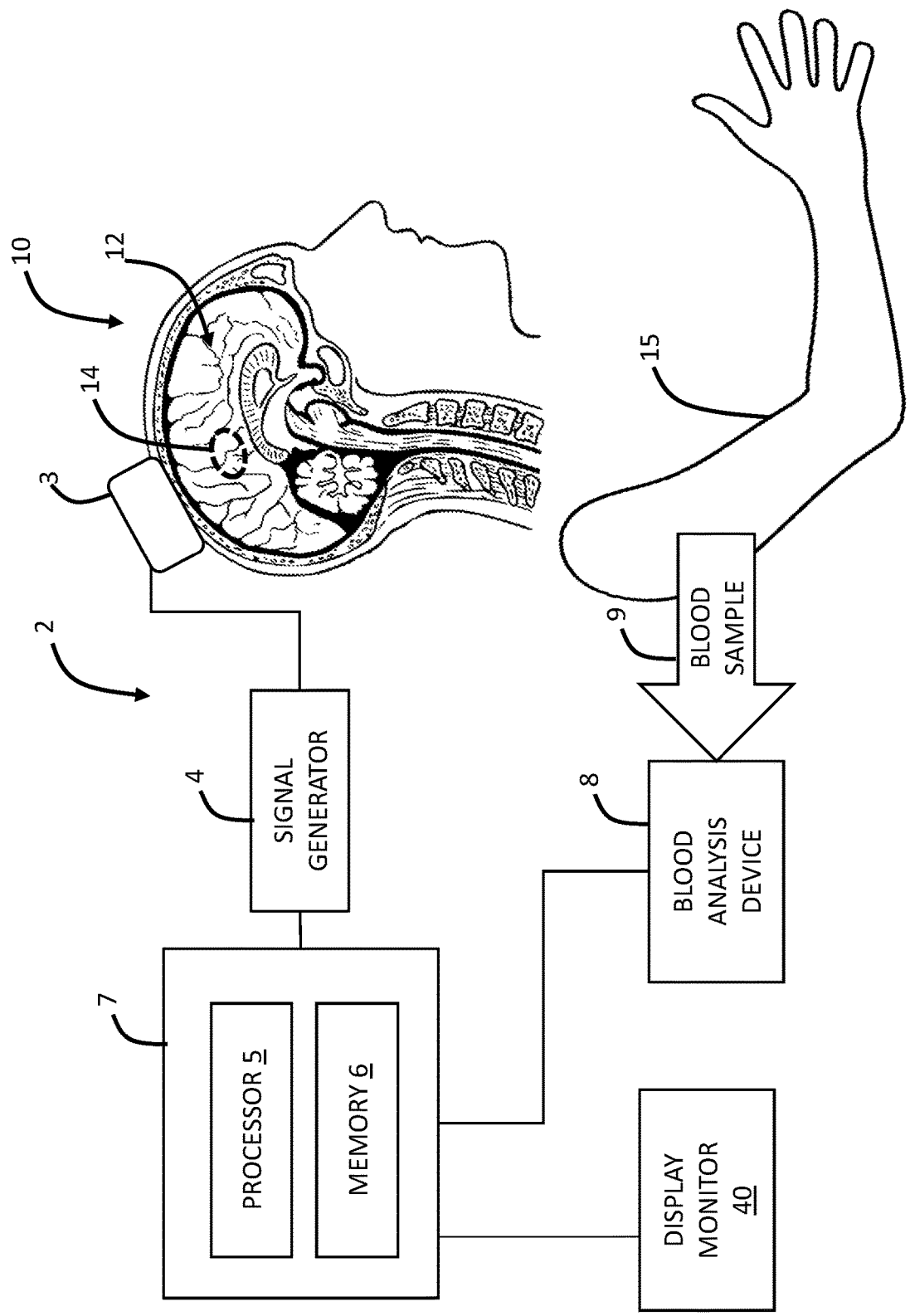
FIG. 1A schematically shows a BB disruption system in accordance with an embodiment of the disclosure.

Applying PEFs at sufficiently high EF strength results in electroporation (EP), in which an electrical potential is induced across the cell membrane sufficient to create nanoscale pores in the lipid bi-layer, thus permeabilizing the cell membrane. The effect of EP depends on factors such as tissue type, cell size and pulse parameters including pulse strength, shape, duration, number of pulses, and frequency. EP can be subdivided into reversible EP (RE) in which the cell membrane returns to its default non-permeabilized state over time, and irreversible EP (IRE), typically induced at higher EF strengths than what is needed for RE induction, in which the cell does not recover from permeabilization and the cell eventually undergoes cell death.

As disclosed in the present disclosure, PEFs can also induce BB disruption in which permeability of the BB is increased independent of, and without requiring, electroporation. We studied this phenomenon in detail using an in vitro BBB model, in vivo animal studies, and computational modeling, as described herein below. It was unexpectedly discovered that increased BB permeability can be obtained by applying a train of PEFs characterized by low-intensity EF strengths (at field strengths substantially lower than the threshold for inducing electroporation, even RE, by way of example 100 V/cm or less), as well as a low frequency (by way of example 10 Hz or less) and/or a low pulse count (by way of example 100 or less). PEFs at EF strength required to induce IRE and thermogenic tissue damage is known to be even higher than for inducing RE. As such, it was also unexpectedly discovered that PEFs that are sufficiently low in EF strength can induce BB disruption while avoiding electroporation (RE or IRE) as well as damage, such as thermal damage, that can be associated with higher level of field strength required to induce IRE or RE, and while also avoiding large total injections of charge that result from high pulse count and/or high frequency EF stimulation. PEF trains characterized not only by low EF strength, but also by low pulse frequency and/or low pulse counts that are substantially lower than what is typically used for deep brain stimulation, was found to be capable of inducing BB disruption. Without being limited by theory, BB disruption induced by application of BB-disruptive PEFs may be a result of reduction in tight and/or adherens junction protein/s expression and/or function between cells that are connected thereby, by way of example, ECs of CNS blood vessels or choroid plexus capillaries. Without being bound by theory, BB disruption may be mediated by one or more functional changes in one or more protein components of TJs or AJs, by way of example, a conformational change that disrupts extracellular binding of the protein components among themselves or with intracellular scaffolding proteins, protein components being sequestered from the extracellular space between ECs. Without being bound by theory, BB disruption occurs by making available a paracellular pathway between adjacent endothelial cells that is not typically present in a normally functioning BB. Without being bound by theory, BB disruption also occurs by creating a path between endothelial cells for other cells, such as leukocytes, to transmigrate through the BB. The transmigration is optionally an active process, in which the disrupted BB releases a signal that induces cells such as leukocytes to perform the transmigration.

Reference is made to FIGS. 1A-1D. An aspect of an embodiment of the disclosure relates to a method for treating a subject 10 in need thereof, the method comprising: selecting a treatment region 14 within a CNS 12 of the subject, wherein an increased permeability of the BB at treatment region 14 is desired; and applying PEFs (BB-disruptive PEFs) to at least a portion of the brain that is capable of inducing BB disruption in the treatment region.

Reference is made to FIG. 1A, which schematically shows a BB disruption system 2 comprising at least one EF source 3 operatively connected to a signal generator 4. Signal generator 4 comprises or is operatively connected to a processor 5 and a memory 6. Processor 5 and memory 6 are optionally comprised in a computer 7 device that is operatively connected to signal generator 4 to provide BB-disruptive PEFs to a region of CNS 12 of a subject 10 in need thereof. Processor 5 is operable to execute a set of instructions stored in memory 6 to instruct the signal generator to produce a pulse pattern for generating BB-disruptive PEFs in treatment region 14 that is located within CNS 12 of subject 10. As shown in FIG. 1A, treatment region 14 is shown as being located in the brain. However, treatment regions 14 may be located elsewhere in the CNS, including chordate plexus, brain stem, or spinal cord of the subject. The type of BB being disrupted in treatment region 14, which as shown in FIG. 1 is located away from a brain surface and also away from a ventricle, may be a BBB. However, depending on the location of treatment region 14, the BB being disrupted within the treatment region may include a choroidal BCSFB or a meningeal barrier. The at least one EF source 3 may comprise one or more of an electrode or a source of a changing magnetic field that is configured to be placed in close proximity to, on, or within CNS 12.

Optionally, BB-disruptive PEFs are generated by a train of electrical pulses induced in the CNS by one or more electrodes. At least one electrode of the one or more electrodes is optionally placed inside CNS tissue, on a surface of the brain (or brainstem or spinal cord), subcutaneously, of the skull, on a surface of dura mater surrounding the CNS, intranasally, endoscopically, or intravascularly.

Optionally, BB-disruptive PEFs are induced in the treatment region by a non-invasive EF source placed external to the skull of the subject. Optionally, the EF source is an external electrode placed on a scalp of the subject. Optionally, the EF source is a source of a changing magnetic field, by way of example a TMS device, a conductive coil, or an antenna.

In an embodiment of the disclosure, the strength of an EF (which may be referred to as the "treatment field strength") induced at the treatment region by application of BB-disruptive PEFs by EF source 3 is sufficient to induce BB disruption in at least a portion of treatment region 14. The treatment field strength is optionally between 148 V/cm and 0.5 V/cm, between 80 V/cm and 2 V/cm, between 60 V/cm and 2 V/cm, and about 55 V/cm. Optionally, the treatment field strength is less than 148 V/cm, less than 100 V/cm, less than 80 V/cm, less than 70 V/cm, less than 60 V/cm, less than 50 V/cm, less than 20 V/cm, less than 10 V/cm, less than 9 V/cm or less than 8 V/cm. Optionally, the treatment field strength is at least 0.5 V/cm, 2 V/cm or 5 V/cm. Optionally, duration of an individual PEF is between 10 nanoseconds (10 ns) and 10 milliseconds (ms), between 1 microsecond and 1 ms, or between 10 microseconds and 100 microseconds. Optionally, BB-disruptive PEFs comprise a single pulse or a train of a plurality of PEFs between 2 and 1000 pulses, between 50 and 500 pulses, between 2 and 100 pulses, between 2 and 50 pulses, between 2 and 20 pulses, between 2 and 10 pulses, or less than 10 pulses. In an embodiment of the disclosure, the PEFs are applied at a frequency of less than 75 Hz, less than 50 Hz, less than 20 Hz, less than 10 Hz, less than 5 Hz, less than 2 Hz, about 1 Hz, or less than 1 Hz. Optionally, the frequency is between about 4 Hz and about 1 Hz. Optionally, the frequency of the PEF train is at least 0.5 Hz. In a more particular embodiment, BB-disruptive PEFs comprise a train of PEFs at a frequency of between 1 Hz and 10 Hz, each PEF having a field strength in the treatment region of between 5 V/cm and 100 V/cm, optionally between 40 V/cm and 60 V/cm.

In an embodiment of the disclosure, the BB-disruptive PEFs are applied to a treatment region such that a maximum EF strength anywhere in the CNS during application of BB-disruptive PEFs, which may be referred to as the "brain-wide field maximum", is below threshold for inducing thermal damage and/or electroporation (RE or IRE). Optionally, the treatment field strength is equal to or less than the brain-wide field maximum, and is optionally less than 280 V/cm, less than 200 V/cm, less than 190 V/cm, less than 175 V/cm, less than 150 V/cm, less than 100 V/cm, less than 50 V/cm, less than 20 V/cm, or less than 10 V/cm.

A first EF intensity threshold for induction of electroporation as well as lower second threshold EF intensity for induction of BB disruption each depend on various features of the applied PEFs including but not limited to EF strength, frequency, pulse count, pulse shape, and pulse duration. The first and second thresholds may also respectively depend on features of CNS tissue to which the PEFs are applied, including but not limited to age of the subject, health of the subject, the anatomical CNS region(s), and orientation of a cell membrane with respect to the PEFs. In addition, the relationship between a strength of an energy output generated at EF source 3, by way of example voltage (V) where the EF source is an electrode or Gauss (G) where the EF source is source of a changing magnetic field, is dependent on configuration of the particular type of EF source 3 being used and where elements of the EF source is located relative to the treatment region at the time of PEF application. As such, control signals to be sent from computer device 7 to signal generator 4 for EF source 3 to generating BB-disruptive FEPs in accordance with an embodiment of the disclosure may be generated, optionally by processor 5 executing a set of instructions stored in memory 6, based on to one or more of the above-noted features characterizing one or more of: a desired treatment field strength, anatomical location of treatment region 14, properties of EF source 3, and the location(s) of EF source 3 relative of treatment region 14.

Application of BB-disruptive PEFs is optionally preceded or followed by administration of a therapeutic agent for treating a CNS disorder. Optionally, the therapeutic agent is a "BB impermeable" agent whose extravasation from a CNS blood vessel into CNS tissue or CSF is blocked or retarded by a normally functioning BB. The therapeutic agent may be administered in an amount sufficient to have the therapeutic agent be introduced into a CNS bloodstream of the subject, such that a therapeutically effective amount of the therapeutic agent reaches the target region provided that the BB is disrupted by BB-disruptive PEFs. Optionally, the therapeutic agent is administered locally in or near the treatment region. Alternatively or additionally, the therapeutic agent is administered systemically, for example orally or parenterally into the bloodstream of the subject.

Optionally, the treatment region is at a different location from the intended target of action for the therapeutic agent. By way of example, a therapeutic agent intended to treat an infection or disorder in the brain may be administered in accordance with the following protocol: (1) the therapeutic agent is administered systemically, optionally through a parenteral, intravenous, or oral route; and (2) BB-disruptive PEFs suitable for disrupting a meningeal barrier located at a portion of the spinal cord is applied at the spine. As a result of this protocol, the therapeutic agent will be expected to enter the CSF in the subarachnoid space of the portion of the spinal cord where the PEFs were applied, and diffuse along the spinal cord, up to the brain of the subject. By way of example, such a method may be used to less invasively administer an anti-migraine medication to a subject suffering from a migraine, or administer an antibiotic agent to a subject suffering from bacterial meningitis.

Optionally, the therapeutic agent is administered at a time point relative to BB-disruptive PEF application, so that blood concentration of the therapeutic agent at the treatment region is maximal at the time in which the BB disruption is maximal. Optionally, the therapeutic agent is administered at a time point relative to BB-disruptive PEF application so that blood concentration of the therapeutic agent at the treatment region stays above a predetermined threshold while BB disruption is still in effect, in order to mitigate clearing of previously extravasated therapeutic agent back into the bloodstream. The timing can be determined based on the route of administration and the identity of the therapeutic agent the impact the blood pharmacokinetics of the therapeutic agent, as well as parameters of the BB-disruptive PEFs that influence the time course of BB-disruption. Optionally the time point can be pre-determined or determined responsive to calibration by imaging (for example MRI) and/or blood assays.

Optionally, the therapeutic agent is an antimicrobial agent or an analgesic agent. Optionally, the therapeutic agent is a chemotherapeutic agent or an immunotherapeutic agent optionally for treatment of cancerous growth in the brain. Examples of chemotherapeutic agents include cisplatin, carboplatin, paclitaxel, temozolamide, 5-fluorouracil, mitomycin C, methotrexate, hydroxyurea, cyclophosphamide, dacarbazine, mitoxantrone, an anthracyclin (by way of example epirubicin or doxorubicin), taxotere, tamoxifen, irinotecan, an anti-estrogen, and an interferon. Examples of immunotherapeutic agents include an immune checkpoint inhibitor, an antibody, a peptide, a cytokine, an interleukin, a vaccine, and a chimeric antigen receptor (CAR). Optionally, the therapeutic agent is a nanoparticle. Optionally, the therapeutic agent is a gene therapy agent comprising a nucleic acid polymer. Optionally, the therapeutic agent is an agent for treating an essential tremor, a stroke, an aneurism, hypoxia, or a neurodegenerative disease, by way of example Alzheimer's disease, Parkinson's disease, multiple sclerosis, amyotrophic lateral sclerosis, or Huntington's disease. Optionally, the therapeutic agent is a cell for a cell-therapy application. The cell is optionally a tumor-infiltrating lymphocyte, a dendritic cell or a differentiated/undifferentiated monocyte.

Computer device 7 is optionally configured to initiate application of BB-disruptive PEFs by EF source 3 responsive to registration of a signal that indicates blood concentration of a therapeutic agent being at a therapeutically effective level. The signal may comprise manipulation of a computer input device (such as a mouse or keyboard; not shown) by a caregiver interacting with a user interface (now shown) of computer device 7 to indicate that blood concentration of the BB impermeable agent is sufficiently high. Optionally, the signal may be generated by computer input device manipulation indicating a time of administration to subject 10 of the BB impermeable agent, and computer device 7 is configured to initiate PEFs application responsive to the signal and a predetermined time delay value so that the PEFs are applied at a time when blood concentration of the BB impermeable agent is expected to be at a therapeutically effective value.

Optionally, BB disruption system 2 comprises a blood analysis device 8 operable to detect a blood concentration of a given therapeutic agent in a blood sample 9 taken from subject 10, optionally from an arm 15 of the subject. Computer device 7 may be operatively connected with blood analysis device 8, and be configured to initiate application of BB-disruptive PEFs by EF source 3 responsive to a signal from blood analysis device 8 indicating that the blood concentration of the BB impermeable agent is above a predetermined threshold.

Optionally, BB-disruptive PEFs are applied to a subject having a CNS disorder associated with abnormal accumulation of a macromolecule in CNS tissue, such that BB disruption is sufficient to increase clearance of the macromolecule from CNS tissue into a CNS bloodstream through the BB within the treatment region. Optionally, the CNS disorder is Alzheimer's disease and the macromolecule is a beta amyloid protein peptide or a tau protein peptide.

FIG. 1B schematically illustrates an embodiment of EF source 3 comprising at least one intracranial electrode 20 operatively connected to signal generator 4 (not shown) that is placed through a burr hole (not shown) in skull 16 of the subject into CNS 12 at or near treatment region 14. Intracranial electrode 20, once inserted into the desired location in the CNS, is activated by signal generator 4 (not shown) to induce EF pulses, schematically illustrated by a thunderbolt 22, to induce PEFs in treatment region 14. One or more external electrodes 24 is optionally be applied extracranially, for example on a scalp 18, skull, or dura mater of the subject, to serve as ground. Alternatively or additionally, intracranial electrode 20 comprises a ground electrode as well as an energized electrode. Alternatively or additionally, intracranial electrode 20 comprises a multielectrode array. Intracranial electrode 20 and external electrode(s) 24 are placed and the strength of the electric pulse is set as determined by computer device 7 so that the strength of the PEFs applied to the treatment region is sufficient to induce BB disruption in the treatment region. Optionally, the at least one electrode placed inside CNS tissue, on a CNS surface, on the dura mater, or on the skull or spine, is comprised in an implantable device (not shown), which further comprises a power source and a signal generator.

Optionally, intracranial electrode 20 inserted in the desired location at or near treatment region 14 through endoscopic and/or intravascular route. Intracranial electrode 20 may be connected to a portable apparatus comprising a power source, a pulse generator, and a computing device. Optionally, intracranial electrode 20 is comprised in an implantable device comprising one or more of a power source, a pulse generator, and a computing device. Optionally, the implantable device is an implantable intravascular apparatus, optionally comprising an electrode in the form of an endovascular stent or a stent-mounted electrode array.

Optionally, intracranial electrode 20 is comprised in an endoscopic and/or intravascular probe. By way of example, an endoscopic probe configured for CNS tumor removal may comprise an electrode. With such an endoscopic probe, surgical removal of a CNS tumor with the probe may be followed by administration of a chemotherapeutic agent and application of BB-disruptive PEFs by the electrode comprised in the endoscopic probe.

FIG. 1C schematically illustrates an alternative embodiment of EF source 3 for applying BB-disruptive PEFs comprising a plurality of external electrodes 24 that are placed on a skin of subject 10. One or more of the external electrodes serve as energized electrodes, schematically illustrated by a thunderbolt 22, and the remaining external electrodes serve as ground. External electrodes 24 may be placed as appropriate by a caregiver or as determined by computer device 7 (not shown) and the strength and pattern of electric pulse 22 applied to the one or more selected external electrodes may be determined by computer device 7 (not shown) so that the strength of the PEFs applied to the treatment region (not shown) is sufficient to induce BB disruption in the treatment region. While FIG. 1C shows external electrodes 24 being placed on a scalp of the subject for inducing BB disruption in the brain, external electrodes 24 may optionally be placed behind the neck of the subject to induce BB disruption in the brainstem, or be along the spine of the subject to induce BB disruption in the spinal cord.

Optionally, the electrical pulses applied by intracranial electrode 20 (as shown in FIG. 1B) or external electrode(s) 24 (as shown in FIG. 1C), are characterized by any one or combination of the following: the electrical pulses comprise a plurality of DC electrical pulses having a duration of between 10 nanoseconds (10 ns) and 10 milliseconds (ms), and the electrical pulses comprise an AC signal, each pulse corresponding to a peak of the AC signal. Optionally, the electrical pulses may be a waveform having one or more of the following polarities: square, triangular, trapezoidal, exponential decay, sawtooth, sinusoidal, and alternating.

FIG. 1D schematically illustrates an alternative embodiment of EF source 3 for applying BB-disruptive PEFs comprising a magnetic field source 30, by way of example a conductive coil, an antenna, or a TMS device, which is configured to be placed external to subject 10 and generate a changing magnetic field, schematically illustrated by dotted lines 32, which induces an EF in treatment region 14 via electromagnetic induction. Optionally, the changing magnetic field 32 is applied as a train of magnetic field pulses, which induces a train of PEFs in treatment region 14. The shape, number, and placement of magnetic field source 30 may be determined by a caregiver or computer device 7, and the strength and pattern of magnetic field 32 may be determined by computer device 7 (not shown) so that the strength of the PEFs induced in treatment region 14 is sufficient to induce BB disruption in the treatment region.

Example 1

In Vitro Model of BBB

Figure 2A:
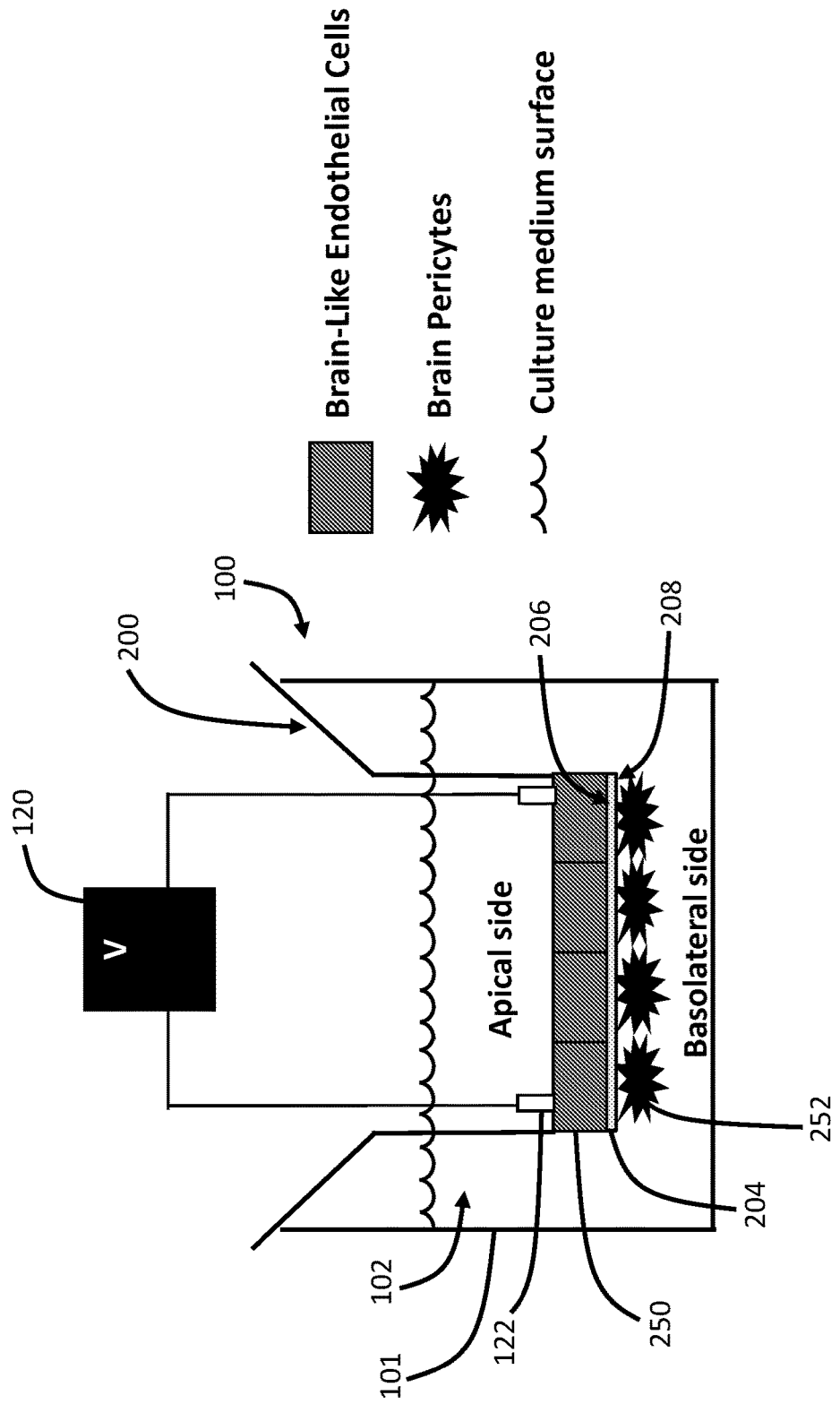
FIG. 2A schematically illustrates an in vitro BB model.

Reference is made to FIG. 2A that schematically illustrates an in vitro BBB model 100 grown in Transwell inserts 200 (3401-Costar, Corning, USA). The in vitro human BBB model was generated as follows: $CD34^+$-derived ECs 250 were seeded onto matrigel-coated (BD Biosciences, USA) apical side 206 of a Transwell insert membrane 204. Primary bovine brain pericytes 252 were seeded on the gelatin-coated basolateral side 208 of the same Transwell inserts 2-24 h before the seeding of the ECs. The co-culture system grown on membrane 204 of Transwell insert 200 was maintained in a cell culture well 101 filled with ECM medium 102 and allowed to grow under standard tissue culture conditions over 6-8 days for the ECs to acquire BLEC (brain-like EC) properties and for the combined culture to acquire BBB properties. The BLECs expressed TJs and transporters typically observed in brain endothelium and maintain expression of most in vivo BBB properties for at least 20 days. Based on the configuration of the cells being grown in the model, the apical side of the Transwell insert emulates a luminal side of a BBB and the basolateral side of the Transwell insert emulates an abluminal side of a BBB. BLEC and pericytes were grown in ECM growth medium (Sciencell, USA) consisting of 5% fetal calf serum (Gibco, USA), ECGS supplements and 500 µg/ml gentamycin (Biological industries, Israel). The BBB cultures were treated with an application of electric pulses (10×50 µs pulses at 1 Hz) generated by a signal generator 120.

PEFs were applied to Transwell inserts 200 using an electroporator power supply (BTX 830; Harvard Apparatus, Holliston, MA). Custom designed platinum iridium electrodes 122 (0.68 cm apart, electrode length 0.9 cm) placed on the apical side of Transwell insert 200 were used for Transwell experiments. For each Transwell insert 200, 10 pulses with a duration of 50 µs pulses at 1 Hz were applied. Pulse amplitudes ranged between 5V and 100V for low voltage experiments and between 200 V and 2000V for high voltage experiments. For control, electrodes were placed inside the TW insert but no pulses were applied. Given the parameters of the electrode and based on a finite elements model of the described system, the EF generated between the electrodes by the applied voltage can be approximated as uniform across the ECs monolayer and can be calculated by dividing the Voltage by the electrodes distance. Given the setup of the in vitro BBB model, the relationship between the voltage (in V) applied to the electrical pulses and the EF intensity (in V/cm) of the resulting PEFs applied to the in vitro BBB model can be approximated as 1 V per 1.48 V/cm, as shown in Table 1.

TABLE 1

| Pulse voltage (V) | EF intensity (V/cm) |
|---|---|
| 5 | 7.4 |
| 10 | 14.8 |
| 15 | 22.2 |
| 20 | 29.4 |
| 40 | 58.8 |
| 50 | 73.5 |
| 60 | 88.2 |
| 80 | 117.6 |
| 100 | 148 |
| 500 | 735.3 |
| 600 | 882.4 |
| 800 | 1176.5 |
| 1000 | 1470.6 |

The effect of PEFs application on the BBB in-vitro model, including BBB disruption, was measured in various ways, as described herein below.

Example 2

PEF-Induced BBB Disruption Measured with Sodium Fluorescein Permeability Assay

Figure 2B:
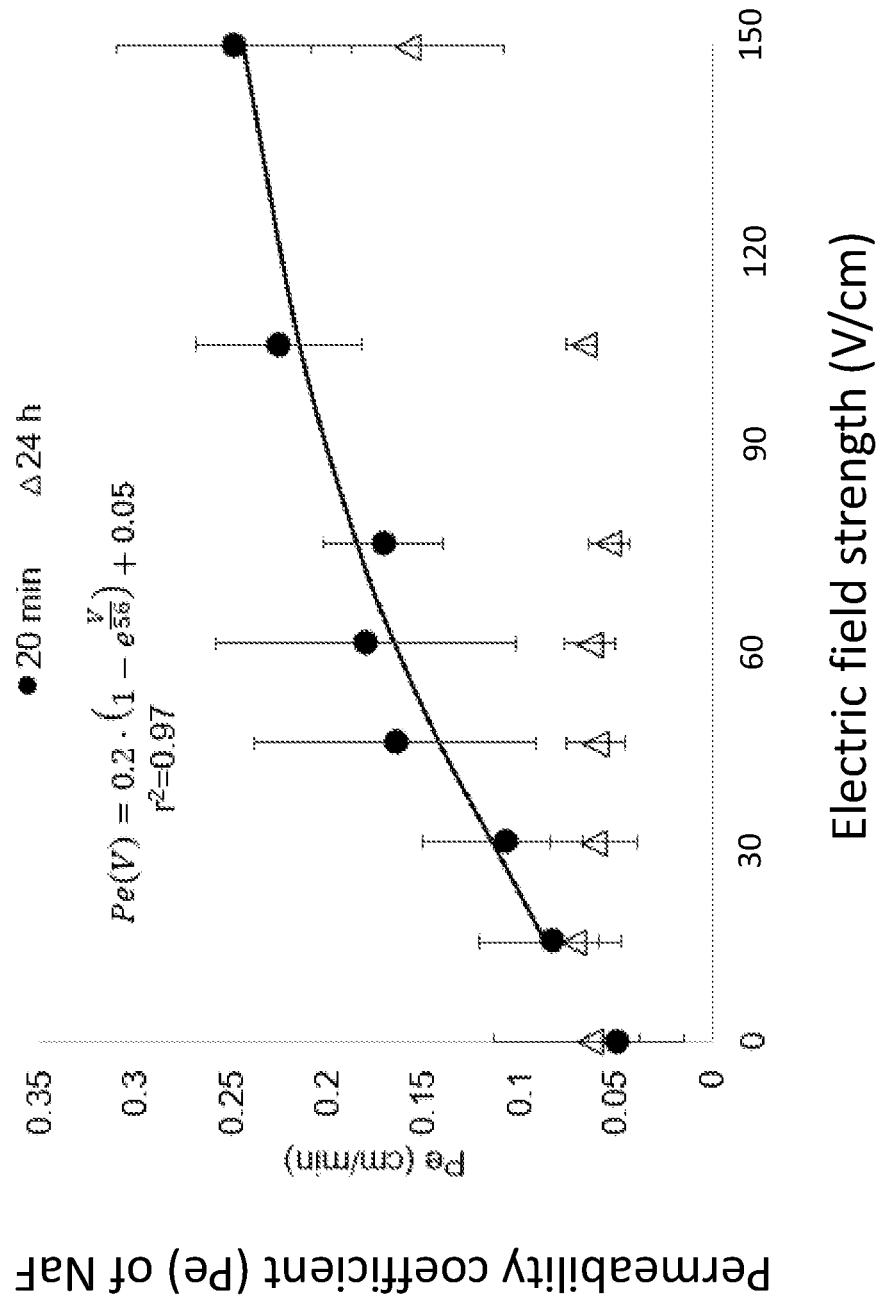
FIG. 2B shows results of sodium fluorescein (NaF) permeability assay through the BBB model after PEF application in accordance with embodiments of the disclosure.

Reference is made to FIG. 2B, which shows the results of permeability measurements for paracellular marker sodium fluorescein (NaF), made 20 minutes (min) following PEFs application (filled circles) and 24 hours following PEFs application (open triangles).

50 µl of a solution containing 0.5 mg/ml NaF in PBS was added to the luminal (apical) side of each Transwell insert 200 one minute prior to PEFs application. PEFs were applied to the cells from the apical side as described above. Immediately after PEFs application, the plates were placed in a darkened incubator for 20 min with mild agitation. A sample of medium 102 collected from under basolateral side 208 was collected and the samples' fluorescence was measured using TECAN pro200 plate reader (485/538 nm excitation/emission). In order to study the recovery of the barrier, the permeability assay was repeated 24 hours later in the same inserts (the medium was replaced with fresh medium after the 20 min permeability assay). N=6-12 Transwell inserts for each voltage field strength.

The endothelial permeability coefficient (Pe) in cm/min was calculated as follows: The clearance principle was used to obtain a concentration-independent transport parameter. The average volume cleared was plotted versus time, and the slope was estimated by linear regression. Both insert permeability (PSf, for insert only coated with collagen) and insert plus endothelial cell permeability (PSt, for insert with collagen and cells) were taken into consideration according to the following formula (1):

$$\frac{1}{PS_e} = \frac{1}{\frac{1}{PS_t} - \frac{1}{PS_f}} \quad (1)$$

To obtain the endothelial permeability coefficient (Pe) of the molecules (in cm/min), the permeability value for the endothelial monolayer was divided by the surface area of the porous membrane of the insert (1.13 cm³).

We found that increased permeability of in vitro BBB model 100 for NaF could be induced by application of PEFs at unexpectedly low EF intensities, well below the electroporation threshold. Increased NaF permeability without induction of electroporation is an indication of BBB disruption. A 40±9% increase in permeability was already visible at an extremely low EF intensity of 14.8 V/cm (10 V applied to electrodes 122). The permeability continued to rise with the increase in EF intensity of the applied PEFs. For example, as shown in FIG. 2B, application of PEFs at low field intensities such as 148 V/cm (100 V applied to electrodes 122), 74 V/cm (50 V applied to electrodes 122), or 22.2 V/cm (15 V applied to electrodes 122), increased permeability of the in vitro BBB model for NaF. The results were fitted to an inverse exponent function (2):

$$Pe(V) = 0.2\left(1 - \frac{V}{e^{56}}\right) + 0.05 \quad (2)$$

($r^2$=0.97, p<0.0001). Therefore, BBB disruption would be expected to be induced at even lower PEFs intensities, for example 5 V/cm, 2 V/cm, 1 V/cm or 0.5 V/cm.

ANOVA was used to compare permeability coefficients Pe for each PEF train treatment (20 min after treatment; closed circles as shown in FIG. 2A) and control conditions without PEFs application. Since Kolmogorov-Smirnov test rejected normality (p<0.0001) a logarithmic transformation was performed as described above, after which normality was obtained. Results of the ANOVA revealed a statistically significant main effect, F(7,97)=33, p<5E-24, ω2=0.73. Post hoc dunnett t' test indicated that there was a significant difference between the control group (without PEFs application) to each of the treatment field strengths. The results are summarized in Table 2 (below).

The same analysis was conducted for the Pe coefficients calculated from the 24 h experiments (open triangles as shown in FIG. 2A). Since Kolmogorov-Smirnov test rejected normality (p<0.0001) a logarithmic transformation was performed as described above, after which normality was obtained. Results of the ANOVA revealed a statistically significant main effect, F(6,60)=6.6, p<1.7E-20, ω2=0.81. These results show that approximately 81% of the total variation in permeability were attributable to differences in the treatment voltages. Post hoc dunnett t' test indicated that there was no difference between the control and the groups treated with voltages below 100 V, indicating that the barrier function of the in vitro BBB model completely recovered by 24 hours following PEFs application at field strengths less than 148 V/cm. The results are summarized in Table 2 (below).

TABLE 2

| EF strength (V/cm) | Pe @20 min | Pe @24 h |
|---|---|---|
| 0 | 0.05 ± 0.01 | 0.06 ± 0.04 |
| 15 | 0.08 ± 0.03** | 0.07 ± 0.01 |
| 30 | 0.1 ± 0.04*** | 0.06 ± 0.02 |
| 45 | 0.16 ± 0.07*** | 0.06 ± 0.02 |
| 59 | 0.18 ± 0.07*** | 0.06 ± 0.01 |
| 74 | 0.17 ± 0.03*** | 0.05 ± 0.01 |
| 103 | 0.22 ± 0.04*** | 0.07 ± 0.007 |
| 148 | 0.25 ± 0.06*** | 0.15 ± 0.04* |

Mean ± SD and p values of post hoc tests.
*p < 0.05,
**p < 0.01,
***p < 0.0001

Example 3

Figure 2C:
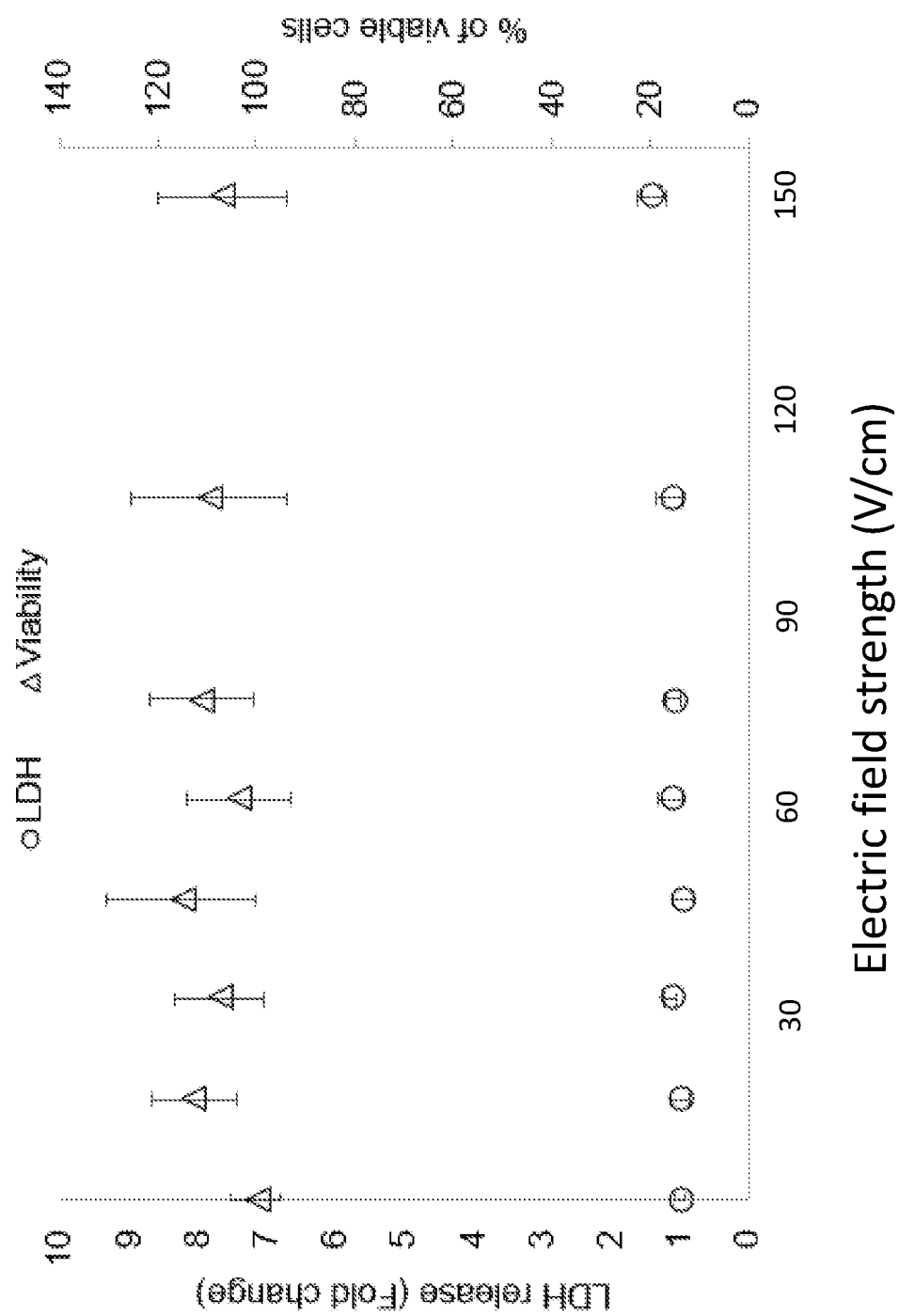
FIG. 2C shows results of Lactate dehydrogenaz (LDH) and PrestoBlue viability assays of ECs in the BBB model after PEF application in accordance with embodiments of the disclosure.

BBB Disruption Induced By Low Field-Strength PEFs Does Not Require Electroporation Reference is made to FIG. 2C, which shows the effect of PEFs application between 10 V and 100 V on cell viability as assay with presto blue (open triangles) and on induction of electroporation as assayed with Lactate dehydrogenase (LDH). The viability of the cells treated with PEFs with field strengths of 15 V/cm to 148 V/cm was assessed using the presto blue assay conducted one hour post-PEFs application. 35 µl Presto blue was added to the luminal side of the Transwell insert one hour post-PEFs application and the wells were incubated at 37° C. for 30 min. Media from the apical compartment was then read with Spectra Max fluorescence plate reader (560 nm excitation, 590 nm emission). ANOVA clearly indicated that there was no decrease in viability (N=at least 6 Transwell inserts for each PEF train condition, F(7,56)=1.6, p=0.16), suggesting no irreversible damage.

Because the presto blue viability assays revealed no cell death at field strengths of 148 V/cm or less, we measured the LDH levels in the medium after PEF train application in order to assess whether BBB disruption can be explained by EP of the EC's membranes. Lactate dehydrogenase (LDH) assay was used to determine whether the PEFs induced EP in in vitro BBB model 1. LDH is a stable cytosolic enzyme with a molecular weight of 144 kDa that is released from the cell upon membrane disruption. LDH kit (CytoTox 96® Promega) was used for this assay. One hour post-PEF train application, 50 µl of the apical medium of each TW insert was transferred to a 96 well plate and equal amount of CytoTox 96 Reagent was added to each well and incubated for 30 min. Stop Solution was then added, and the absorbance signal was measured at 490 nm with TECAN pro200 (Tecan Trading AG, Switzerland) plate reader. N=at least 3 Transwell inserts for each field strength. The results were compared to the viability assay.

ANOVA with Dunnett t' test post hoc analysis revealed no significant increase in LDH levels (by a factor of 1.4±0.2) below 148 V/cm (ANOVA F(7,53)=7.7, p<2E-5, Dunnett t' for 148 V/cm group p<5E-8) indicating that BBB disruption could not be attributed to EP at PEFs having a field strength of less than 148 V/cm.

Example 4

PEF Train-Induced BBB Disruption Measured with TEER

Figure 3A:
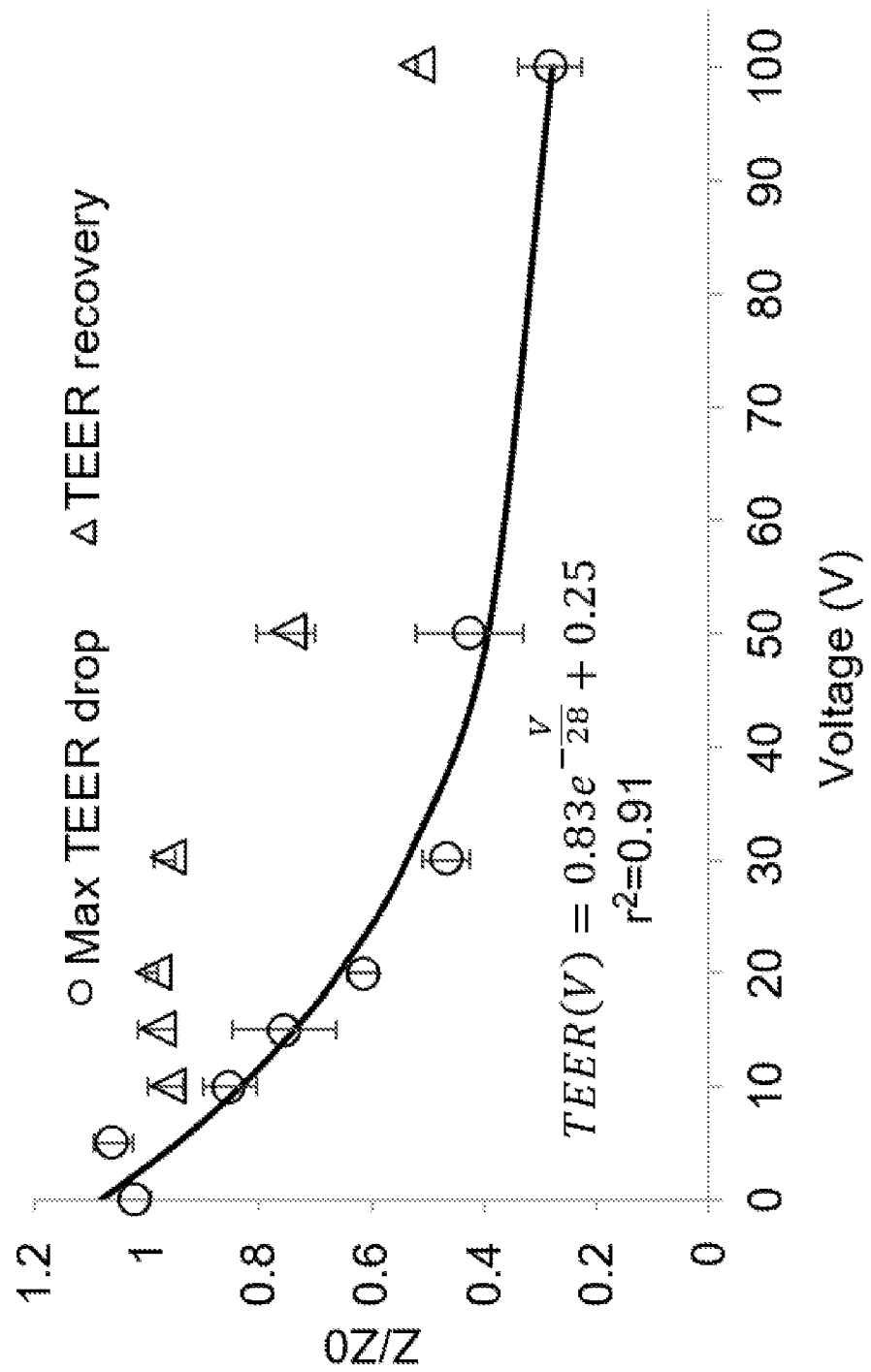
FIGS. 3A-3B show results of impedance change and transendothelial electrical resistance (TEER) measurements of the BBB model after PEF application in accordance with embodiments of the disclosure.

Reference is made to FIG. 3A, which shows the results of transendothelial electrical resistance (TEER) measurements that were carried out with in vitro BBB model 100. TEER reflects impedance to the passage of small ions through the physiologic barrier of the BBB and is recognized as one of the most accurate and sensitive measures of BBB integrity. A decrease in TEER reflects increased permeability and loss of barrier function. TEER of the Transwell insert with the in vitro BBB model was recorded using an Endohm™ chamber (WPI) connected to an EVOM™ resistance meter (WPI) or using the CellZscope™ apparatus (NanoAnalytics) that records TEER values automatically over time.

Samples of in vitro BBB model 100 were treated with PEFs using the same setup used in Example 2, comprising signal generator 120 and plate electrodes 122, and TEER was extracted from the modulus and phase of an impedance spectrum measured for each sample prior to and one minute following application of PEF trains (10 pulses with pulse duration of 50 µs at 1 Hz) at different pulse voltages. The average TEER prior to PEF train application was 48±4.4 Ω*cm². The average TEER after 100V reduced to 8.6±2.5 Ω*cm². The TEER measurement for each tested pulse amplitude, normalized to steady state TEER prior to PEF train application, is shown in Table 3 below:

TABLE 3

| Electrode voltage (V) | 0 | 10 | 20 | 30 | 50 | 100 |
|---|---|---|---|---|---|---|
| Electric field (V/cm) | 0 | 14.8 | 29.4 | 44.4 | 73.5 | 148 |
| Normalized TEER (Z/Z0) | 1 | 0.85 | 0.62 | 0.47 | 0.42 | 0.28 |

Figure 3B:
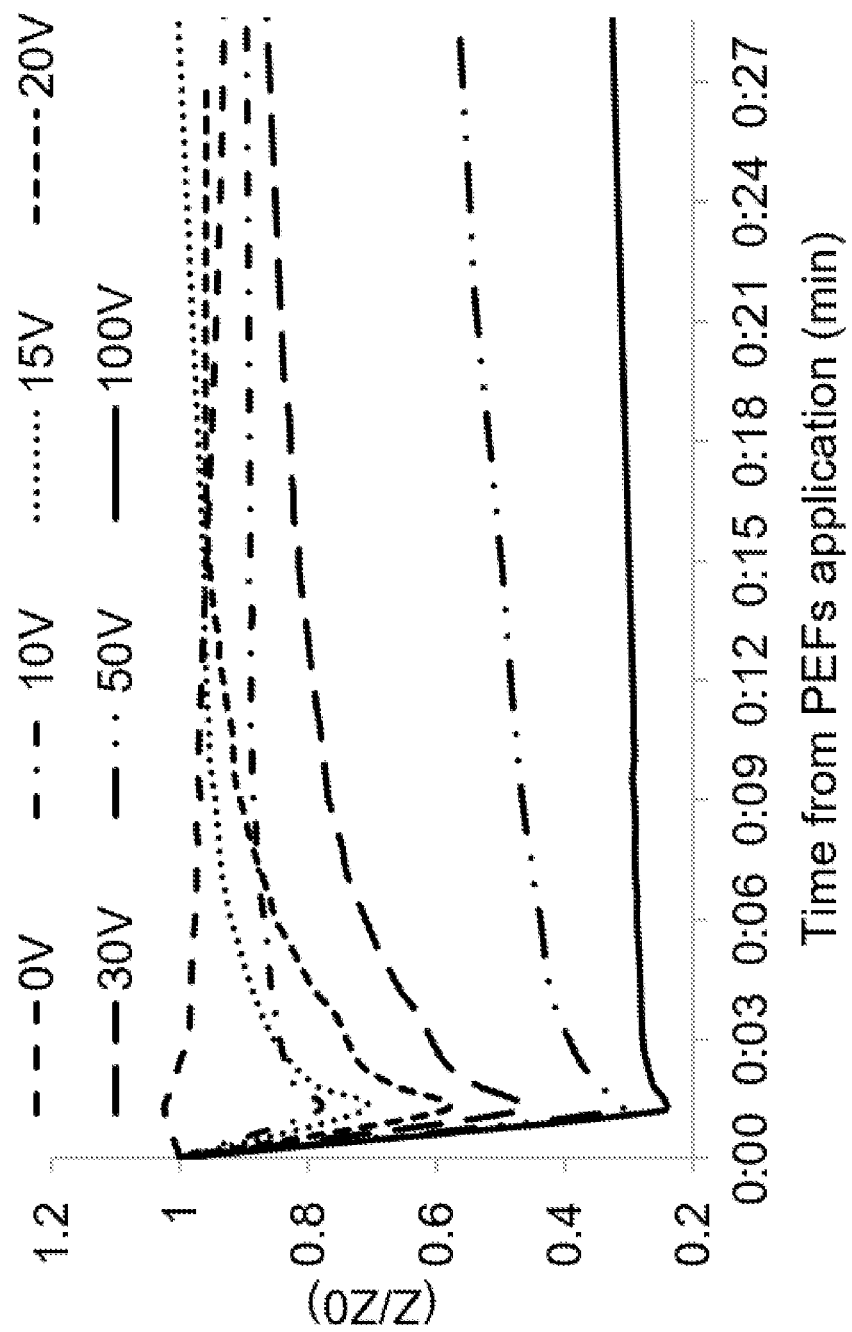

As shown in FIG. 3A, permeability of in vitro BBB model 100 as measured by TEER was dependent on the intensity of the applied EF. TEER decreased by 16±5% compa10red to baseline within one minute following application of PEFs at a field strength of 14.8 V/cm. The TEER continued to decrease with increasing treatment voltages. The results showed an exponential behavior ($r^2$=0.95. p<0.0001) suggesting convergence towards higher voltages. (FIG. 3B). The results were fitted to a function (3):

$$TEER(V) = 0.83e^{-\frac{V}{28}} + 0.25 \qquad (3)$$

($r^2$=0.95. p<0.0001). ANOVA was used to compare fold change in TEER immediately post PEF train application for different treatment voltages. The test revealed a statistically significant main effect, F(7,18)=72.8 p<6.6E-12, ω2=0.94. These results show that approximately 94% of the total variation in TEER were attributable to differences in the treatment voltages. Post hoc comparisons, using the dunnett t' test demonstrated that TEER was significantly decreased compared to control in voltages starting from 15 V/cm.

Reference is made to FIG. 3B. In all tested PEF trains, the PEF-induced reduction in TEER was already maximal at the first measured time point of 1 minute post-PEF, after which the TEER gradually recovered. A significant inverse correlation was found between the decrease in TEER after 1 min and the increase in permeability (Pearson, r2=0.91, p<0.0001). Full recovery (return to over 95% of baseline TEER) was observed in all cultures treated with field strengths below 73.5 V/cm (50V). Partial recovery (return to 75%±0.05% of baseline) of the TEER was obtained at 73.5 V/cm (50V) and no recovery of TEER was observed at 148 V/cm (100 V). The recovery process was completed within 30 min in most cases with no correlation between the time to recovery and the pulses voltage. Following the initial recovery, there was no significant change in TEER until the termination of the experiments 24 h post PEF train application.

Example 5

Transmigration of Immune Cells Across the BBB

Figure 4:
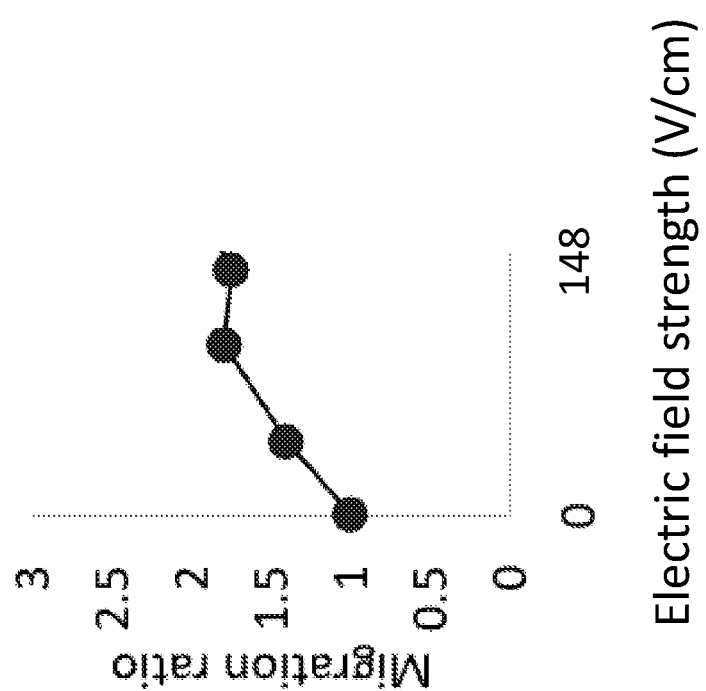
FIG. 4 shows results of a leukocytes transmigration assay through the BBB model after PEF application in accordance with embodiments of the disclosure.

Reference is made to FIG. 4, which shows the effects of PEF train application on leukocyte transmigration through in vitro BBB model 100. Fluorescently labeled leukocytes—freshly prepared and fluorescently labeled primary human peripheral blood mononuclear cells (PBMCs)—were added into the apical side of in vitro BBB model 100 and incubated for 24 hours (200,000 cells per Transwell). The Transwell inserts were removed and the relative fluorescence of culture medium on the basolateral compartment was measured using an Infinite 200 PRO™ fluorescence plate reader (Tecan). The BBB is known to hinder transmigration of leukocytes across the EC monolayer of capillaries in the brain. Applying a PEF train (10 pulses with a duration of 50 µs at 1 Hz) to in vitro BBB model 100 at 148 V/cm resulted in an almost two-fold increase compared untreated culture of PBMC transmigration across from the apical to the basolateral compartments both immediately after and 24 hours post-PEF train application. PEFs at an EF strength of 44 V/cm resulted in leukocyte transmigration increasing by 40±7% compared to control conditions. The above results show that BBB disruption reflects increased permeability not only for macromolecules (as shown with NaF assays in Example 2) and ions (as shown with TEER in Example 4), but also for cells by way of example in the context of cell-mediated immune response.

Example 6

Efficacy of Paclitaxel Across the BBB After BBB Disruption

Figure 5A:
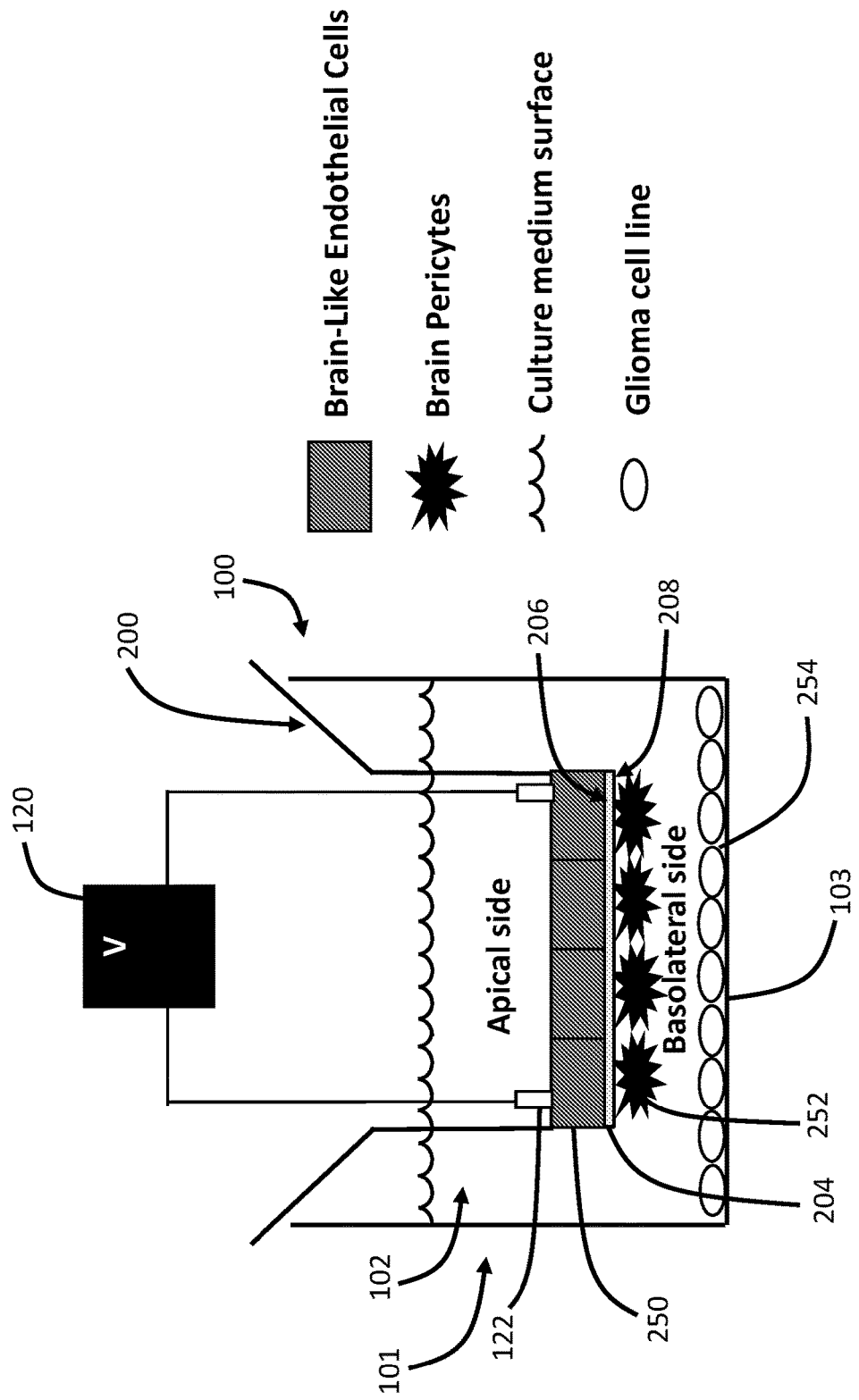
FIG. 5A schematically illustrates a in vitro BBB model comprising a glioma cell line.

Reference is made to FIG. 5A. To study the effect of PEFs application on BBB permeability for Paclitaxel (Taxol®), the in vitro BBB model 100 as shown FIG. 2A was modified by seeding a CNS-1 glioma cell line 254 on a bottom surface 103 of cell culture well 101 (40,000 cells per well), into which the BLEC co-culture system grown on membrane 204 of Transwell insert 200 was also grown. When the glioma cell line was at about 16±0.5% confluency, 200 nM Paclitaxel was added into ECM media 102 in the apical side of Transwell insert 200 and PEFs were applied at one of various settings, then incubated for 2 hours after which time the Transwell insert was removed. As a result, any Paclitaxel that did not traverse the Transwell insert during the incubation period was removed along with the Transwell insert, while any Paclitaxel that did traverse the Transwell insert remained in the ECM medium along with the glioma cell line 254. Glioma cell line 254 was then further incubated for three days and the level of confluency was measured at 2 hours, 1 day, 2 days, and 3 days following Paclitaxel administration.

Figure 5B:
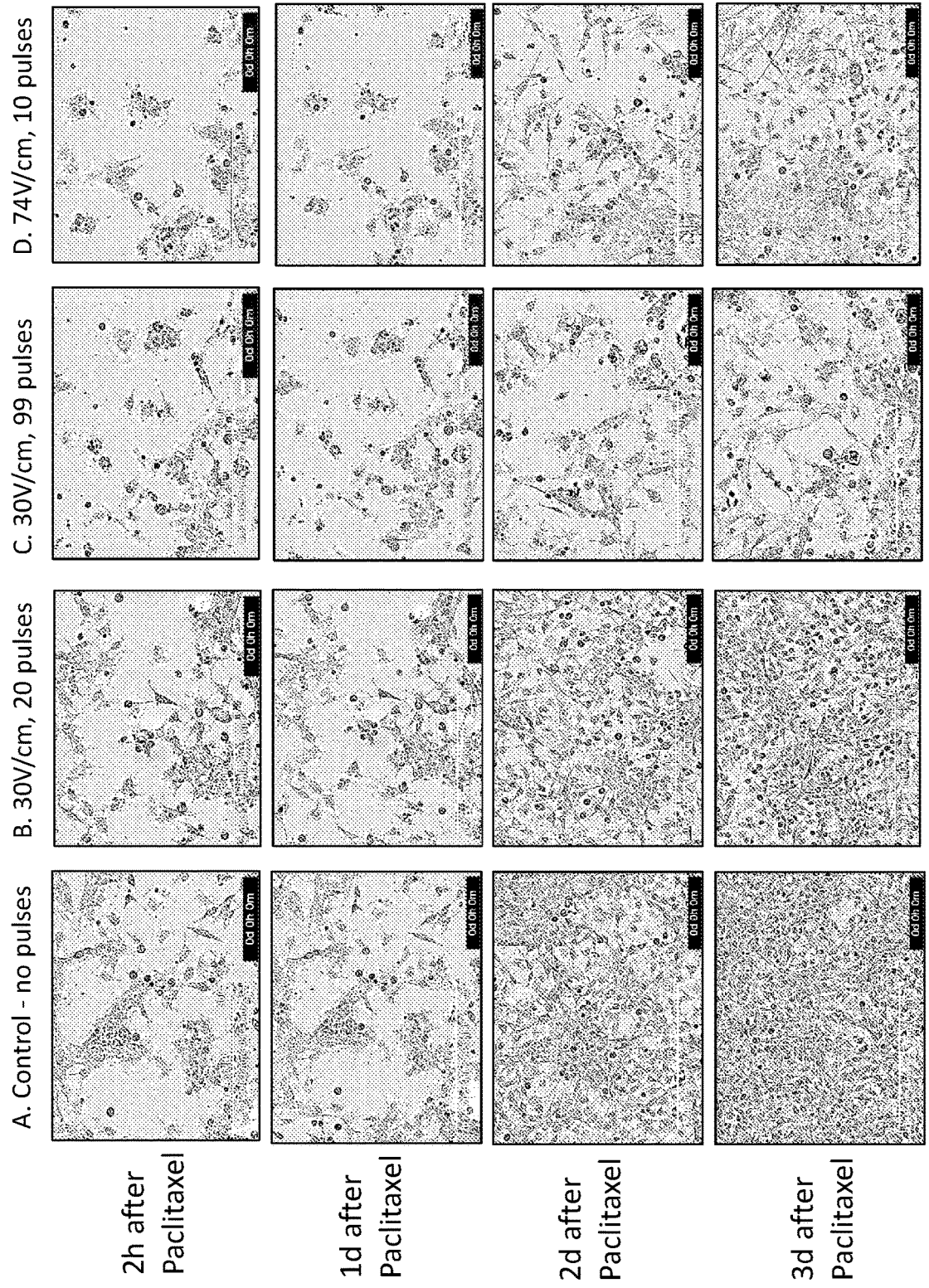
FIG. 5B shows exemplary results of an efficacy study with paclitaxel applied through the BBB model after PEF application in accordance with embodiments of the disclosure.

The results as shown by way of example in FIG. 5B indicate that low pulse-count, low frequency, low EF strength PEFs induce sufficient BBB disruption to allow a therapeutic dose of Paclitaxel to traverse the in vitro BBB model and reach the glioma cell line. FIG. 5B shows a table of representative images of glioma cell line 254 at various stages (Rows 1-4 respective showing: 2 hours after Paclitaxel administration; 1 day after Paclitaxel administration; 2 days after Paclitaxel administration; and 3 days after Paclitaxel administration) after co-incubation with a BBB-model treated with various PEF application conditions (Columns A-D respectively showing: Control with no PEF application; 20 pulses with field strength of 30 V/cm at 1 Hz; 99 pulses of PEFs with field strength of 30 V/cm at 1 Hz; and 10 pulses of PEFs with field strength of 74 V/cm at 1 Hz). When the BBB model is not treated with PEFs (FIG. 5B, column A), the glioma cells grow normally and reach full confluency after 3 days, indicating that no (or an insignificant amount of) Paclitaxel was able to traverse the BBB model. By contrast, application of 10 pulses of PEFs at a field strength of 74 V/cm (FIG. 5B, column D) caused sufficient BBB disruption to allow a therapeutic dose of Pactlitaxel to reach the glioma cell line and substantially disrupt its growth. Application of 20 pulses of PEFs at a field strength of 30 V/cm (FIG. 5B, column B) was less effective and glioma growth was not significantly retarded. However, a longer pulse train of 99 pulses at the same field strength of 30 V/cm (FIG. 5B, column C) induced sufficient BBB disruption to allow a therapeutic dose of Paclitaxel to reach the glioma cell line, such that the level of retardation of glioma growth was equivalent to application of 10 pulses of PEFs at a field strength of 74 V/cm (FIG. 5B, column D). These results also indicate that relatively low-EF strength PEFs can achieve similar therapeutic effects as relatively high-strength PEFs when the low-strength PEFs are applied over a higher count of pulses.

The ability to compensate for weaker BBB induction from lower field strength PEFs by increasing the pulse count may be advantageous when there it is desirable to minimize the field strength of BBB-inducing PEF trains. By way of example, in order to achieve a given treatment field strength in a treatment region located in an interior brain region through an extracranial EF source, a more surface region of the brain that is closer to the EF source may experience a higher electrical field strength that is sufficiently high to induce electroporation. Applying a high-count train of PEFs may be used to achieve BB-disruptive PEF trains that results in both (1) a sufficient degree of BBB disruption in the treatment region and (2) a brain-wide field maximum that is below the threshold for electroporation and/or thermogenic damage.

Example 7

Low-Intensity, Low Frequency, Low Pulse Count PEF Train Induces BBB Disruption In Vivo Reference is made to FIGS. 6A-6D. An adult male rat underwent craniotomy and dura removal and then underwent PEF train treatment as follows: A signal electrode (a round plate electrode ~0.8 cm in diameter) was pressed against the exposed brain and a rectangular ground electrode plate electrode (3 cm×5 cm plate) was placed under the rats' body, below its head and chest. 10 pulses (pulse duration of 50 µs at 2 Hz), with a pulse voltage of 100 V, were applied to the exposed brain.

Figures 6A, 6B, 6C, 6D:
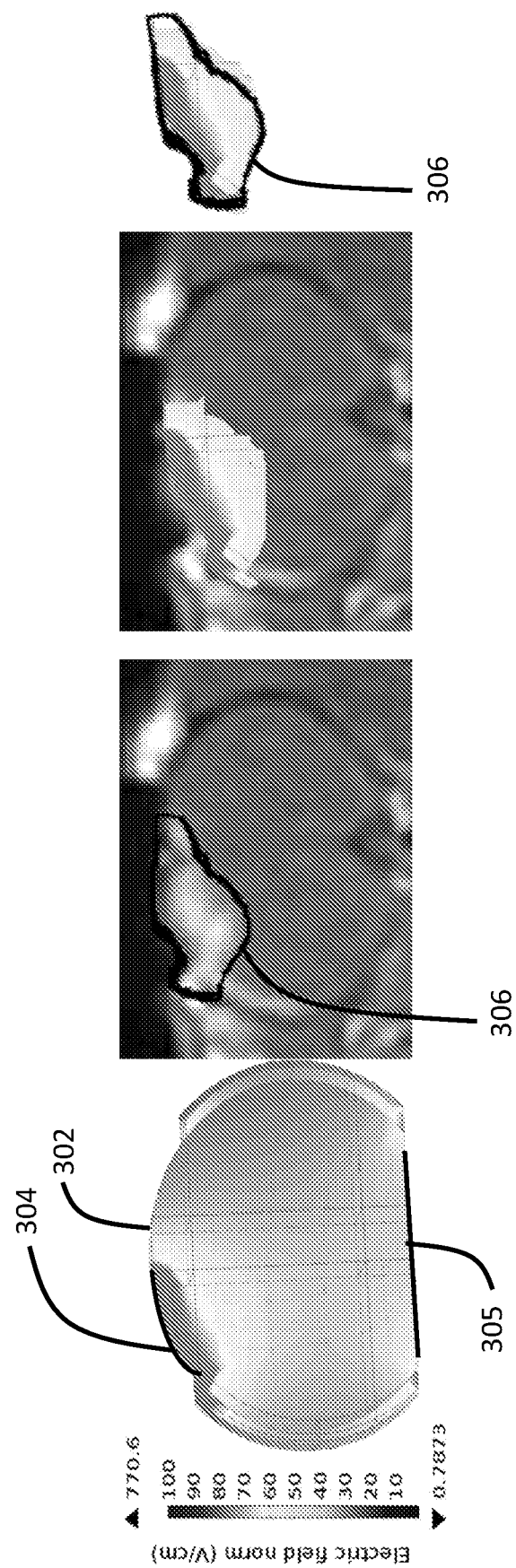
FIG. 6A shows EF distribution calculated using a finite elements model of a rat head after applying PEF treatment in accordance with an embodiment of the disclosure.
FIG. 6B shows a contrast-enhanced T1-weighted MRI image obtained immediately following PEF treatment in accordance with an embodiment of the disclosure.
FIG. 6C shows the calculated EF distribution as shown in FIG. 6A overlaid onto the T1-weighted MRI image as shown in FIG. 6B.
FIG. 6D shows the calculated EF distribution as shown in FIG. 6A overlaid onto portion of the T1-weighted MRI image as shown in FIG. 6B, bounded by an outline that schematically shows the region of the brain in which BBB disruption was detected.

FIG. 6A shows Electrical field distribution calculated using a finite elements model of a rat head after applying 100V on the active electrode using 2 surface electrodes. The active electrode, indicated as a dark line 304, was modeled as a small round electrode placed directly on the brain surface. The ground electrode, indicated as a dark line 305, was modeled as sheet electrode pressed underneath the head and chest.

FIG. 6B shows a contrast-enhanced T1-weighted MRI image obtained immediately following PEF train treatment. The location and shape of the enhancement on the T1 image (white) corresponds to the location of BBB disruption in the brain, and black outline 306 schematically shows the boundary of the region of the brain in which BBB disruption was detected.

FIG. 6C shows the calculated EF intensity as shown in FIG. 6A overlaid onto the T1-weighted MRI image as shown in FIG. 6B. FIG. 6D shows the calculated EF distribution as shown in FIG. 2A overlaid onto portion of the T1-weighted MRI image as shown in FIG. 6B, bounded by outline 306 that schematically shows the region of the brain in which BBB disruption was detected. The overlays indicate that the shape and volume of BBB disruption induced by the PEF train treatment corresponds to the finite element model calculation of the intensity of the induced EF, and that BBB disruption was obtained at electrical field intensities as low as 50 V/cm to 60 V/cm.

Example 8

Low-Intensity, Low Frequency PEF Train Induces BBB Disruption In Vivo

Mice were anesthetized prior to experiment and remained under full anesthesia for the duration of experiment and scans. A midline scalp incision was made and extended until exposure of lateral aspects of skull bone was achieved. Two plate electrodes (1.5 cm×1.5 cm) covered with conductive gel were pressed against the skull and electric pulses were applied (99-400 pulses at 100-250V, 50 µs pulse duration with a frequency ranging from 1-4 Hz.).

The mice were then transferred to an MRI system to image the brain. Gadolinium (Gd)-based contrast agent was injected intravenously at a dosage of 400 µl/kg immediately prior to a first T1-weighted MRI scan. Each mouse was scanned for 45 min with repetitive T1-weighted MRI scans as well as T2-weighted MRI scan and Susceptibility-weighted (SWAN) MRI scans to ensure that no edema and bleeding occurred.

For each mouse, all T1-MRI scans acquired were registered to the 1st T1-MRI scan following contrast agent injection, using a 3D rigid registration algorithm. The 1st series following contrast agent injection was subtracted from the delayed series. This analysis resulted in "Treatment response assessment maps" (TRAMs), in which negative signal represents contrast clearance while positive signal represents contrast accumulation. The method enables detection of subtle BBB disruption as well as slow accumulation of contrast agent and whole brain BBB disruption. Positive signal indicates subtle BBB disruption while negative signal indicates vasodilatation or very short-term BBB disruption with fast wash in and wash out of contrast agent/drugs.

Figure 7A:
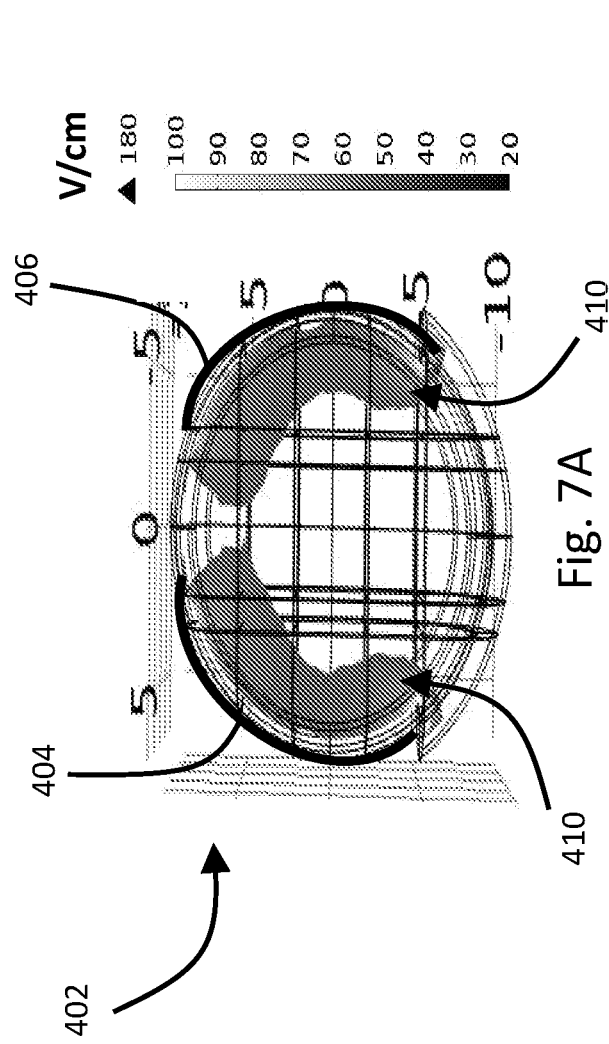
FIG. 7A shows a simulated electrical field distribution in a mouse head that is expected after applying PEF treatment in accordance with an embodiment of the disclosure, as calculated using a finite elements model of a mouse head.

PEF-induced BBB disruption was detected via TRAMs but not by conventional T1 MRI visualization. It was found that intensity and volume of in vivo BBB disruption correlated to electrode stimulation intensity as well as number of pulses. Reference is made to FIG. 7B, which shows a TRAMs MRI image of the mouse brain after application of a 200-pulse train of 100 V pulses at 4 Hz. The image is a subtraction of an image acquired 3 minutes post treatment from an image acquired 45 min post treatment. The image indicates that the applied pulse train was sufficient to induce BBB disruption as detected by TRAMs.

A finite elements model of electrical properties of a mouse brain was used to render a simulation of EF distribution (in V/cm) expected in the mouse brain during the PEF treatment. Reference is made to FIG. 7A, which shows a rendered image 402 of expected electrical field distribution in a mouse head after application the 200-pulse train of 100 V pulses at 4 Hz from a pair of place electrodes 404, 406. Simulated image 402 showed that the pulse train is expected to result in zones 410 of PEF induction, the PEFs having an EF strength about 55 V/cm within zones 410. Based on shape and location, zones 410 corresponds to a region of the mouse's cerebral cortex, at both hemispheres.

Figure 7C:
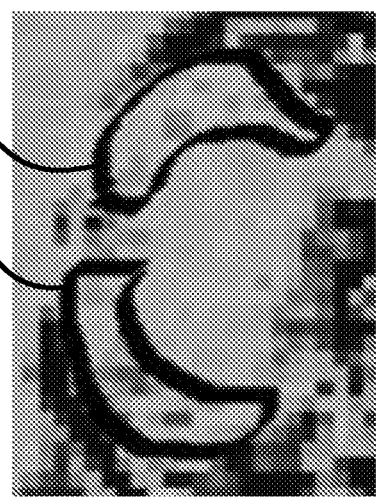
FIG. 7C shows the TRAMs MRI image as shown in FIG. 7B bounded by an outline that schematically shows the region of the brain in which BBB disruption was detected based on the TRAMs MRI image.
Figure 7B:
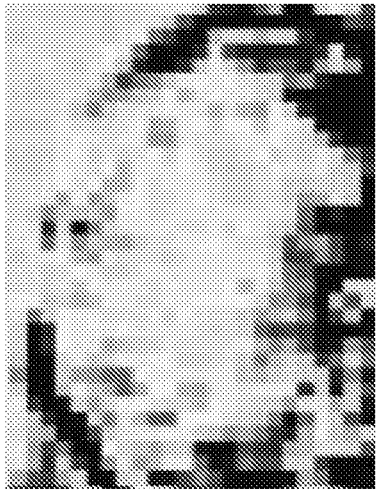
FIG. 7B shows a slice of a TRAMs MRI image obtained following a PEF treatment in accordance with an embodiment of the disclosure.

Reference is made to FIG. 7C, which shows the TRAMs MRI image as shown in FIG. 7B bounded by outlines 420 that schematically show the region of the brain in which BBB disruption was detected based on the TRAMs MRI image.

When rendered image 402 as shown in FIG. 7A was overlaid with the corresponding TRAMs MRI image as shown in FIG. 7B, it was found that application of the 100 V electrical pulses and the resulting induction of PEFs of about 55 V/cm in the region of the mouse's cerebral cortex was sufficient to induce BBB-disruption in the intact brain.

Simulating higher-voltage stimulation resulted in an expectation of higher-EF strength and/or larger-volume regions of PEFs being induced in the brain, as determined by the finite elements model. In addition, more extensive BBB disruption from the higher-voltage stimulation was confirmed, as determined by TRAMs MRI imaging. By way of example (not shown), stimulation with 150V pulses (200 pulses, 4 Hz) was expected according to the model to result in PEFs of about 80 V/cm covering a similar region of the mouse cortex, while TRAMs MRI imaging of a mouse treated with the 150V pulses (the image being a subtraction of an image acquired 3 minutes post treatment from an image acquired 45 min post treatment) confirmed that a higher degree of BBB-disruption was achieved.

Given the robustness of BBB disruption by PEFs at a field strength of 55 V/cm, it is expected that lower-strength PEFs, by way of example 40 V/cm or 20 V/cm would also successfully induce BBB-disruption as detected by TRAMs imaging. In addition, it is understood that weaker induction of BBB-disruption, even while present, would not pass a threshold for detection by TRAMs MRI imaging.

Figure 8B:
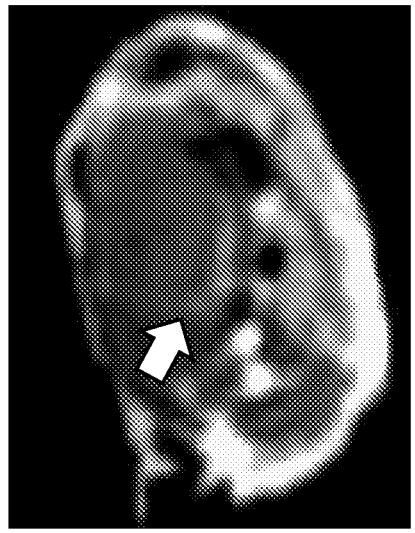
FIGS. 8A-8D shows T1 weighted MIR images of mouse brains showing a ventricle, following a PEF treatment in accordance with an embodiment of the disclosure.
Figure 8D:
Figure 8A:
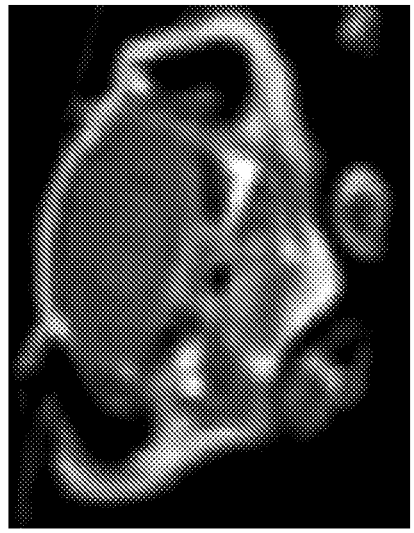
Figure 8C:

Reference is made to FIGS. 8A-8D. T1 weighted MRI images with contrast agent of ventricles in mice receiving the plate electrode treatment at the same parameters that induced BBB disruption, as shown by way of example in FIGS. 7A-7C, also revealed enhancement of the contrast agent at the ventricles. The enhancement at the ventricles is indicated by a block arrow in each of FIGS. 8B-8D. FIG. 8B shows a T1 weighted MRI image of the ventricle following 100 V stimulation (200 pulses, 4 Hz). FIG. 8C shows a T1 weighted MRI image of the ventricle following 150 V stimulation (200 pulses, 4 Hz). FIG. 8D shows a T1 weighted MRI image of the ventricle following 200 V stimulation (200 pulses, 4 Hz). This result indicates that exposure to a train of PEFs with a same or similar parameter suitable for inducing disruption of BBB at the cortex was also able to induce disruption of BCSFB at the ventricles.

There is therefore provided a brain barrier disruption system comprising: an electric field source operable to generate an electric field in a CNS of a subject; a signal generator operable to activate the electric field source; and a computer device comprising a processor and a memory, and operatively connected to the signal generator, wherein the processor operates when executing a set of instructions stored in the memory to: register activation parameters suitable for the electric field source to generate a pulsed electric fields at a frequency of 10 Hz or less, wherein the pulsed electric fields are expected to have an electric field strength of less than 148 V/cm within a treatment region located in the CNS, where increased permeability of a brain barrier selected from a blood-brain barrier or a blood-cerebrospinal fluid barrier is desired; and transmit control signals to the signal generator suitable to activate the electric field source in accordance with the activation parameters. Optionally, the processor operates when executing the set of instructions to determine the activation parameters based on one more target settings selected from: a set of stereotactic coordinates of the treatment region, one or more properties of the electric field source, and respective locations of one or more electric field-generating elements of the electric field source relative of the treatment region. Optionally, the activation parameters are predetermined activation parameters saved in the memory.

Optionally, the brain barrier is a blood-brain barrier. Optionally, the treatment region is located in a CNS region selected from the group consisting of: a brain, a brainstem, a choroid plexus, and a spinal cord.

Optionally, the pulsed electric fields are expected to have an electric field strength of less than 100 V/cm, less than 60 V/cm, or less than 20 V/cm within the treatment region. Optionally, the pulsed electric fields comprise between 2 and 1000 pulsed electric fields. Optionally, the pulsed electric fields are expected to have an electric field strength of less than 280 V/cm throughout the CNS of the subject.

Optionally, the electric field source comprises one or more electrodes and/or a magnetic field source configured to generate a magnetic field. Optionally, the one or more electrodes comprises at least one of the following: an intracranial electrode, a skin electrode, a subcutaneous electrode, a sub-skull electrode, or a subdural electrode. Optionally, the one or more electrodes consists of a plurality of skin electrodes.

In an embodiment of the disclosure, the electric field source, the signal generator, and the computer device are comprised in an implantable device. Optionally, the implantable device is an intracranial implantable device, an intracavity implantable device, an intranasal implantable device, an intraspinal implantable device, or an intravascular implantable device.

In an embodiment of the disclosure, the electric field source is comprised in an intravascular probe.

In an embodiment of the disclosure, the electric field source is comprised in an endoscopic probe. Optionally, the endoscopic probe is configured for brain tumor removal.

In an embodiment of the disclosure, the processor operates, when executing the set of instructions, to generate a visualization of an anticipated region of increased permeability of the brain barrier based on the determined activation parameters.

In an embodiment of the disclosure, the computer device operates when executing the set of instructions to active the electric field source responsive to a computer input signal that provides sufficient information to determine a time or an expected time of a blood concentration of a therapeutic agent exceeding a predetermined threshold, so that increased permeability of the brain barrier induced by the pulsed electric fields coincides with the blood concentration of a therapeutic agent exceeding the predetermined threshold.

There is also provided a method for treating a subject in need thereof, the method comprising: selecting a treatment region within a CNS of the subject, where an increased permeability of a brain barrier selected from a blood-brain barrier or a blood-cerebrospinal fluid barrier is desired; and applying pulsed electric fields with an electric field source to at least a portion of the brain at a frequency of 10 Hz or less, wherein the pulsed electric fields are expected to have an electric field strength of less than 148 V/cm within the treatment region. Optionally, the brain barrier is a blood-brain barrier. Optionally, the treatment region is located in a CNS region selected from the group consisting of: a brain, a brainstem, a choroid plexus, and a spinal cord. Optionally, the treatment region comprises a portion of the spinal cord, and the brain barrier is a blood-cerebrospinal fluid barrier.

In an embodiment of the disclosure, the treatment region comprises an excess of a substance that is expected to enter a CNS bloodstream at the treatment region upon the permeability of the brain barrier in the treatment region being increased. Optionally, the substance is associated with a neurodegenerative disorder. Optionally, the neurodegenerative disorder is Alzheimer's disease, and the substance comprises a beta-amyloid peptide.

Optionally, the pulsed electric fields are expected to have an electric field strength of less than 100 V/cm, less than 60 V/cm, or less than 20 V/cm within the treatment region. Optionally, the pulsed electric fields comprise between 2 and 1000 pulsed electric fields. Optionally, the pulsed electric fields are expected to have an electric field strength of less than 280 V/cm throughout the CNS of the subject.

Optionally, the electric field source comprises one or more electrodes and/or a magnetic field source configured to generate a magnetic field. Optionally, the one or more electrodes comprises at least one of the following: an intracranial electrode, a skin electrode, a subcutaneous electrode, a sub-skull electrode, or a subdural electrode. Optionally, the one or more electrodes consists of a plurality of skin electrodes.

In an embodiment of the disclosure, the electric field source, the signal generator, and the computer device are comprised in an implantable device. Optionally, the implantable device is an intracranial implantable device, an intracavity implantable device, an intranasal implantable device, an intraspinal implantable device, or an intravascular implantable device.

In an embodiment of the disclosure, the electric field source is comprised in an intravascular probe.

In an embodiment of the disclosure, the electric field source is comprised in an endoscopic probe. Optionally, the endoscopic probe is configured for brain tumor removal.

In an embodiment of the disclosure, the method further comprises administering a therapeutic agent to the subject in an amount and route sufficient to have the administered therapeutic agent be introduced into a bloodstream of the subject, wherein: the pulsed electric fields sufficiently increase brain barrier permeability so that a therapeutic amount of the therapeutic agent traverses the brain barrier from the CNS blood vessel to a CNS region in the treatment region. Optionally, the pulsed electric fields are applied responsive to when a blood concentration of the therapeutic agent exceeds or is expected to exceed a predetermined threshold, so that increased permeability of the brain barrier induced by the pulsed electric fields coincides with the blood concentration of a therapeutic agent exceeding the predetermined threshold. Optionally, the therapeutic agent is for treating a CNS disorder. Optionally, the CNS disorder is selected from the group consisting of: an essential tremor, a stroke, an aneurism, hypoxia, and a neurodegenerative disease. Optionally, the neurodegenerative disease is selected from the group consisting of: Alzheimer's disease, Parkinson's disease, multiple sclerosis, amyotrophic lateral sclerosis, or Huntington's disease. Optionally, therapeutic agent is an antimicrobial agent, an analgesic, an agent for treating a neurodegenerative disorder, a chemotherapeutic agent for treatment of cancerous growth in the brain, an immunotherapeutic agent, a nanoparticle, a nucleic acid polymer, or a cell. Optionally, the chemotherapeutic agent is selected from the group consisting of: cisplatin, carboplatin, paclitaxel, temozolamide, 5-fluorouracil, mitomycin C, methotrexate, hydroxyurea, cyclophosphamide, dacarbazine, mitoxantrone, an anthracycline, taxotere, tamoxifen, an antiestrogen, and an interferon. Optionally, the immunotherapeutic agent is selected from the group consisting of: an immune checkpoint inhibitor, an antibody, a peptide, a cytokine, an interleukin, a vaccine, and a chimeric antigen receptor (CAR). Optionally, the cell is a tumor infiltrating lymphocyte, a dendritic cell or a monocyte.

Optionally, the intended target of action of the therapeutic agent is at a different location from the treatment region. Optionally, the treatment region is located at a region of the spinal cord of the subject and the pulsed electric fields increase permeability of a blood cerebrospinal fluid barrier, so that the therapeutic agent traverses the blood cerebrospinal fluid barrier into CSF at the region of the spinal cord.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the disclosure in the present application are provided by way of example and are not intended to limit the scope of the disclosure. The described embodiments comprise different features, not all of which are required in all embodiments of the disclosure. Some embodiments utilize only some of the features or possible combinations of the features. Variations of embodiments of the disclosure that are described, and embodiments of the disclosure comprising different combinations of features noted in the described embodiments, will occur to persons of the art. The scope of the invention is limited only by the claims.

The invention claimed is:

1. A method for treating a subject in need thereof, the method comprising:
   selecting a treatment region within a central nervous system (CNS);
   mounting, on an external surface of the subject, an electric field source that comprises one or both of (i) a plurality of electrodes and (ii) a magnetic field source configured to generate a changing magnetic field; and
   applying a pulsed electric field with said electric field source to at least a portion of the CNS,
   wherein the pulsed electric field has an electric field strength of less than 148 V/cm and a frequency of less than 75 Hz within the treatment region, being below a threshold for inducing electroporation in the treatment region,
   wherein applying the pulsed electric field induces disruptive permeability of a blood brain barrier or a blood cerebrospinal fluid barrier in the treatment region.

2. The method according to claim 1, wherein an electric field strength throughout the brain of the subject is less than 280 V/cm.

3. The method according to claim 1, further comprising administering a therapeutic agent to the subject in an amount and route sufficient to have the administered therapeutic agent introduced into a bloodstream of the subject, so that a therapeutic amount of the therapeutic agent traverses the blood brain or blood cerebrospinal fluid barrier from a blood vessel in the CNS to a region of the CNS in the treatment region when the electric field induces the brain barrier or blood cerebrospinal fluid disruptive permeability.

4. The method according to claim 3, wherein the pulsed electric field is applied responsive to when a blood concentration of the therapeutic agent exceeds or is expected to exceed a predetermined threshold, so that the disruptive permeability of the blood brain or blood cerebrospinal fluid barrier induced by the pulsed electric field coincides with a concentration of the therapeutic agent exceeding the predetermined threshold.

5. The method according to claim 3, wherein the therapeutic agent is an antimicrobial agent, an analgesic, an agent for treating a neurodegenerative disorder, an agent for treating an essential tremor, an agent for treating a stroke, an agent for treating an aneurism, an agent for treating hypoxia, a chemotherapeutic agent for treatment of cancerous growth in the brain, an immunotherapeutic agent, a nanoparticle, a nucleic acid polymer, or a cell.

6. The method according to claim 1, wherein the treatment region is located in a region of the CNS selected from the group consisting of a brain, a brainstem, a choroid plexus, and a spinal cord.

7. The method according to claim 1, wherein the treatment region comprises an excess of a substance that enters a bloodstream in the CNS at the treatment region upon the disruptive permeability of the blood brain or blood cerebrospinal fluid barrier in the treatment region having been increased to a predetermined disruptive permeability.

8. The method according to claim 3, wherein an intended target of action of the therapeutic agent is at a location different from the treatment region.

9. The method according to claim 3, wherein the treatment region is located at a region of the spinal cord of the subject and the pulsed electric field causes disruptive permeability of the blood cerebrospinal fluid barrier, so that the therapeutic agent traverses the blood cerebrospinal fluid (CSF) barrier into the CSF at the region of the spinal cord.

10. The method according to claim 9, wherein the therapeutic agent is for treating an infection or disorder in the brain.

* * * * *